United States Patent [19]

Weissman et al.

[11] Patent Number: 5,614,397
[45] Date of Patent: Mar. 25, 1997

[54] METHOD AND COMPOSITIONS FOR MODULATING LIFESPAN OF HEMATOLYMPHOID CELLS

[75] Inventors: Irving Weissman, Redwood City; Eric Lagasse, Palo Alto, both of Calif.

[73] Assignee: Board of Trustees of the Leland Stanford Junior University, Stanford, Calif.

[21] Appl. No.: 200,016

[22] Filed: Feb. 22, 1994

[51] Int. Cl.⁶ .............................. C12N 15/85; C12N 5/10
[52] U.S. Cl. ........................ 435/172.3; 435/325; 435/355
[58] Field of Search .......................... 435/240.2, 240.21, 435/172.3; 514/44; 424/93.21

[56] References Cited

FOREIGN PATENT DOCUMENTS

WO93/25683  12/1993  WIPO ........................... C12N 15/12

OTHER PUBLICATIONS

Hockenberry et al., "Bcl-2 Functions in an Antioxidant Pathway to Prevent Apoptosis," *Cell* (1993) 75:241–251.

Ellis et al., "Genetic Control of Progammed Cell Death in the Nematode C. elegans," *Cell* (1986) 44:817–829.

Hengartner, M.O., "*Caenorhabditis elegans* gene ced–9 protects cells from programmed cell death," *Nature* (1992) 356:494–499.

Nakayama et al., "Disappearance of the Lymphoid System in Bcl-2 Homozygous Mutant Chimeric Mice," *Science* (1993) 261:1684.

Snouwaert et al., "An Animal Model for Cystic Fibrosis Made by Gene Targeting," *Science* (1992) 257:1083–1088.

Dorin et al., "Cystic fibrosis in the mouse by targeted insertional mutagenesis," *Nature* (1992) 359:211–215.

Lagasse et al., "Cloning and Expression of Two Human Genes Encoding Calcium–Binding Proteins That Are Regulated During Myeloid Differentiation," *Mol. Cell. Biol.* (1988) 8:2402–2410.

Lagasse et al., "Mouse MRP8 and MRP14, Two Intracellular Calcium–Binding Proteins Associated with the Development of the Myeloid Lineage," *Blood* (1992) 79:1907.

Spencer et al., "Controlling Signal Transduction with Synthetic Ligands," *Science* (1993) 262:1019–1024.

Porter et al., "X–Linked Chronic Granulomatous Disease: Correction of NADPH Oxidase Defect by Retrovirus–Mediated Expression of gp91–phox," *Blood* (1993) 82:2196–2202.

Cobbs et al., "Retroviral Expression of Recombinant $p47^{phox}$ Protein by Epstein–Barr Virus–Transformed B Lyphocytes From a Patient With Autosomal Chronic Granulomatous Disease," *Blood* (1992) 79:829–1835.

Erikson et al., "Identification of a Thermolabile Component of the Human Neutrophil NADPH Oxidase," *J. Clin. Invest.* (1992) 89:1587–1595.

DiBartolomeo et al., "Reconstitution of normal neutrophil function in chronic granulomatous disease by bone marrow transplantation," *Bone Marrow Transplantation* (1989) 4:695–750.

Lomax et al., "Selective Defect in Myeloid Cell Lactoferrin Gene Expression in Neutrophil Specific Granule Deficiency," *J. Clin. Invest.* (1989) 83:514–519.

Veis et al., "Bcl–2–Deficient Mice Demonstrate Fulminant Lymphoid Apoptosis, Polycystic Kidneys, and Hypopigmented Hair," *Cell* (1993) 75:229.

Bright et al., *Biosciences Reports*, vol. 14, 1994, pp. 67–81.

Nowicki et al., *Cellular Immunology*, vol. 132, 1991, pp. 115–126.

Sarin et al., *J. Experimental Medicine*, vol. 178, 1993, pp. 1693–1700.

Gong et al., *J. Cellular Phyriology*, vol. 157, 1993, pp. 263–270.

*Primary Examiner*—James S. Ketter
*Attorney, Agent, or Firm*—Karl Bozicevic; Deirdre L. Conley; Fish & Richardson P.C.

[57] ABSTRACT

Methods and compositions for modifying the lifespan of progeny cells of mammalian hematopoietic stem cells, particularly myeloid series cells, are provided. Transgenic non-human mammals also are provided which produce transgenic myeloid cells having an altered lifespan.

10 Claims, 16 Drawing Sheets

```
                                                                                                                                                                                              -1401
TTCCACCTTTGGCTCTTGTAAATAATGTGCTATGAACATGAATGTACAAACATCTGTTGAATCCCTGCATTCAATTC TTTTGCATATATACCCAGGA
                                                                                                                                                                                              -1301
GCAGAATGATGGATCATATGGTAATTCTGTGTTATTTATTGAGGAACAAACTGCGTTTCCATAACAGCTGCACTATTTACATTCCCACTAACAG
                                                                                                                                                                                              -1201
TGCATTAGGCTTCCAATTCTCTATGCCCTCACCAACACTGTTTCTGGGTTTTAAAAGAAGTAGTCATCCTTGTAGGTGTCAGGTGTATCTCATT
                                                                                                                                                                                              -1101
GTCGTTTGCTTCATGTTTCCTAAAGATTAGTAATTTTCATATGCTTATTGACCATTGTATATCTTCTTGGAGAAGTGTCTATTGAGTCTTTCCCC
                                                                                                                                                                                              -1000
AATTTTGATTGGTTTGTTTGTTTTGTTGTTGAGTTGTAGGGATTCTTTATATTCTGGATATTAATCCCTTATCAGATATTTGTTTACAAATATTT
                                                                                                                                                                                              -901
CTTTGTAACAACAGAAACACCACAGTCTTCAAGGTTGGAAGCCAGTTAATCTGAGTAGCATTTGTTAGTGGTGGGAGAGATTTGTTCCTCCTGAA
                                                                                                                                                                                              -801
ATCCTGGGGAATTGGCCACCTCCTCTCTCCTTAGGCATGAAGGCGTCTGGCTTCTCCAAAGAACTCTTCCCCTCCACTACCTCAGAGTTAGCTTCC
                                                                                                                                                                                              -701
TCTCTTCAGCCAGTGATCCTGGGGTCCCAGACACAATAATTAACCAAGAGAGGGTGAAAGCTCCCTGCTGTGTTTATGCAATGGCTCAGGCCCTTGTGA
                                                                                                                                                                                              -601
AGTGCCGAGGGACCCCAAGCAGCCTCCATCCCCAGGGCATTCCCCACAAAGCACCCAAAGAACAACAACGATAGTTTAGTTTTTAGTAATGAGAACAATAGT
                                                                                                                                                                                              -501
GGAATGGATATAGCCCTTGGCAACAACACATTTCCCCACAAAGCACCCAAAGAACAACAACGATAGTTTAGTTTTTAGTAATGAGAACAATAGT
                                                                                                                                                                                              -401
TCTCATGACTAAAAGCCATCAGCCAGGACACTGTTCTCAACCTTTGCGGTCTTTGAAACTCTGACAGAAGCCATGGAGGAATGTTCTCA
                                                                                                                                                                                              -301
CTGAGTGCATGCACTCAAAATGATGCATTCAACTTCAATTCAGTTTCAGGGATGTATGCCTGACCACCAATGCAGGGGATTAGCAATGCAATAGTGGA
                                                                                                                                                                                              -201
GAGGGCATGGGAGTGGGAATCTGGCTGGATCAAGCAAGTGATCAAGCAGCCCAGAAAAA AGAGCCCCCTACCTGCTGTTTTCTTCCTGGGCACTATTG
                                                                                                                                                                                              -101
CCCAGCAAATGCCTTCCTCCTTCCGCTTCTCTCCTACCTCCCCACCCCAAAATTTCATTCTGCACAGTGATT GCCACATTCACTGGTTGAGAAACAGAGACT
                                                                                                                                                                                              -1
GTAGCAACTCTGGCAGGGAGAAGCTGTCTGATGGCCTGGGAAGCTGTGGGCAGCTGGGCAAGCCTAACCGTATAAAAAGGAGCTGCCTCTCAGCCCTGC
┌─────────────┐                                                                                                                                                                             100
│   Exon 1    │
│ATGTCTCTTGTCAGCTGTCTTTCAGAGACCTG│GTAAGTGGGACTGTCTGGGTTGGCCCGCCACTTTGGGCTTCTCTTGGGGAGGGTCAGGGAAGTGGAG
└─────────────┘
              TO FIG. 1B
```

FROM FIG. 1B

AAACCCAAAGGAAGAAAAAGAAATCTATGTTATCCCACCCTACCTCTCACAAGCTTTCCTGCTTACCCTCACCTGGCCTCTGCCCCACATTCCTTCA 1200

GCCCCTCATTCGAGCATTGGATTTGAGGCTTAAGGATTCAAAAAGTCGTCATGAATATAGCTGATGATTTATAGTGGTTCTGAAATGGGTCGGGGATT 1300

TGGGAACAGGGTGGTAGTATAAGAACAACTGATACTGTTCTCTAAGCTAAATCTTAGCTTCCAGTACCTGTCTTAGATGTGGCTCTTGGGAACCTTAGA 1400

GTGATAGCTACATAGAGAAGTGTGTGTGTGGTGTGTGTGTGTCTGTGTGTGTGTGAGAGAGAGACAGAAAGAGAGCAAGAGAGGGAAGGGGGG 1500

AGAGGGCTGATTGTGTGTGTGGTGTGATGTAGGTGGACAATGTTCAGAGTCCTCCATTAACAGGATAATCCTCACACCTGTCCACATACCTGTAGTTGTC 1600

CTTGGGGATTTTGAAAATTTTCCTCCCTCTCCCACTCCCCAACTCCCAAACTCAATTAAATGATAAAGGCAAATAGGCAAATAAATTAGTAAAAC 1700

TTAAGTCAAAGAATAGGTTATTCATACGCTGCCTATGGGATTCTATGCTTTGTGATCAGAAAATTATCTAAAAATACTTCCCAAGGGCTGGTACAAGGG 1800

AGGCCAGAAGACGAGTGGTTCTTCTCTGAGGTGGACATTAAAAAAGAAGAGAAAATGAAGGGGAACCTTTTGACAAGAATGTCACCCCAAACTGGATTTC 1900

ATGCTGTGGTGTGGGGAATTTTCTGTTGTCCTCACTTAGGTGCTGGGGCAGTGGTGTTAGTGATGGGTAAAAAGGTAGGAAGCTGTCACAGAATCACTAA 2000

ACCAGGGGTTCTAACTGTCGTCTATACATCTCTGAAATTGGGTTGAAGTTGTGTGCATCATTTGAGTGACGCACTGAGAACATTCCTCCACGGCTTC 2100

CATCGAGAGTCTCGAAAAGGCCCAACACCTCAAAAAGGTTAAGAACACCTGTCCTGCTTACTGGTTTTTAGTAACAAATGGCAGAGTATTTCTCTGTC 2200

TCTCTCTCTTTTTTTTTTTGAGACACAGGGTCTTGTCTGTCACGTGGACTAGAGTACAATGGCATGATCATGGGCTCACTGTAGCCTCGAA 2300

CACCTGGGCTCAAGTAATCCTCCCACCTCAGCCTCTTAGTAGCTGGGACTACAGCATGAGCCACCACTGCCCTTGGCTAATTTTTAATTATTTTTGTAG 2400

AGATGGAAACTTGCTATGTTGCCAGGCTAGTCTCAAACTCCTGGACTCAAGCGATCCTCCTACCTTGGCCTCCCAAAGTGCTGGGATTACAGTGATC 2500

CACACCACACCTGGCCAAGATTGGAGTATTTTATTGTATTGTTGCTGGGGTGGGTGGGTGTATGCTTTGTGGGGACGTGTTGTTGCCAAG 2600

GGCTAAATCAGTTCCTACCCTGCTGCCCACAGTCCTCTGCCTCTGTGAAGCTAAGGATACACCCGATGATAAGCTGTCAACATA 2695

FIG. 1C

```
ATCACTGTGGAGTAGGGGAAGGGCACTCCTGGGGTGGCAAGGTGGGGCCCTGTGTTCCCACAGTGGGCAGGGAGGTAGTGAAAGGGAAGCTGGC    -901
CGGACAGGAAGGGCCATTCC AAGAGGGCTTTGTGCCAGGGCTAAGCCAAGCTTTCTCCATAGGCAATGGGAGCAACTGGAGGTTCGTAGCAGGAGAAG  -801
GACACATCAAGCCCACCAGGAGCTAAGTAAAACAGTTGTCTCCAAGTTATAAGTTCCTGGAACCCTGTCTGGGAGCAGGATTTAGAAAAATGATGCT    -701
GAGAGATGCTAGAAACATATTCGCCCTGAGGCTCTCTCAGACTGCAAGAGGAAGTATCATCAGAATTCATCAGAACCAGAATAGCTGG            -601
GTCCCCTTCCTGCCAAGTCAGCAACCAGTATGTGACCTTGCTCAGTGTCCATCTCCGGGTGTCAGTTTCT TCATCTACAATGCAAGAGGGTTGCCCACCT  -501
CTGAGAACCCTTCTAACCCCAAATCTCACCCTATGAATCTAAGAACACAACCCCTCGCCATCCTAAGTATCACAGAGCCAGGCAAGCATGGGTGAGAGCT  -401
CAGAGAACCCTCCTTGTTGGACTAAAAGGAAGGGCAGACTGCCATGGGGCAGCCGAGAGGTCAGGCCCCCATAGGTCCTCAGCCTGCTTCAACCTCAAA   -301
GGGGATGGGGGGCTGAGTGGTGCCAGAGGAGCAGAGGCTCGGGGAGAGTAGGGCCTTAGGATAGAAGGGAAATGAACTAAACAACCAGCTTCCTC       -201
CAAACCAGTTTCAGGCCAGGGCTGGGAATTTCACAAAAAGCAGAAGGGCTCTGTGAACATTTCCTGCCCGCCCCTTCTGCCAGCATTAC            -101
CACACTGCTCACCTGTGAAGCAATCTTCCGGAGACAGGGCCAAAGGGCCAAGTGCCCCAGTCAGGAGCTGCTGACACAGCTCTGGC              -1
┌─────────────────────────────────────────┐
│ Exon 1                                  │
│ AAACACTCTGTGTGGCTCCTGGGCTTTG │GTAAGTGAGCTGCCAGCTTCCCCAGGCAGAAGCTGCCTGCCGATTCCTTCTTCCTGACCCAACTT        100
└─────────────────────────────────────────┘
CCTTCCAAATCCTCCTCCTAGAAGCCCTCCTTGGTTGGCCCTGCCTACTTAAAGCTTCTTCACATTTCTTAGGTCATGTTCCCTGGGGCCTCCTGC      200
CCTCAAATGCTTTGCTTTTTGGCACTCTGTAGATATTCTAAAAAATCATTTGTACATGTGTGACAGGCCATCTCCCAGTTAAGTTGCAGCCTGTGCT    300
TTCTTTTATTTGCACTTCCCCCACTATTTCTGTGAGTGCTTAGTAGGAAGTGCAAAGAAGCTTGACAGACATTTTCTTAAGTGTCCCAACTCTTGG     400
```

FROM FIG. 2A

```
                    Exon 2     M  T  C  K  M  S  Q  L  E  R  N  I  E  T  I  I  N  T  F  H  Q  Y  S
                              10                                    20
TTTCCATTACACAG ACAGAGTGCAAGACGATGACTTGCAAAATGTCGCAGCTGGAACGCAACATAGAGACCATCATCAACACCTTCCACCAATACTCTG    500

V  K  L  G  H  P  D  T  L  N  Q  G  E  F  K  E  L  V  R  K  D  L  Q  N  F  L  K
                 30                                    40                                    50
TGAAGCTGGGGCACCCAGACACCCTGAACCAGGGGGAATTCAAAGAGCTGGTGCGAAAAGATCTGCAAAATTTTCTCAAG GTAGGGCTGGACTCTGGCAG    600
GTCTGACCCAGCCTCACCGCAGTTTGGGTTGACAAGGGAGGATGGGAGTATGGGCTACAGCAATCAAGGGGAAGATTTGAGCTCCTGGAGCCCAGCCCA    700
AGACGCAGCGAGTGCCTGTTATACAGGGCAGGTGCTCACAGTTACACAGGACGACAGGGTCAAGAAATTGCTCAATTGAACACCTGCTATTTGTCGGGC    800
CCTGTTCTGGGCAGAGAGGGATGTAGTGGTAAATGGGAGCCCACTATTCCATGAGGAGACACACAGTAAAGTTGTTGGCCAATAAAGAGCACAGATAAAGCC    900
AAATGCCAATAAGTGCCTGGAAGAAAATGAGATAGAGTGCGCTGTGGGCAATGGGCTGTGGGGTGGAGGTGACCAGTTAGGGTACATGAGAAGGGGC   1000
TCTTTGAGGAGGTAACATTTGAGCTGAAGCCCCGAATGTTGGGAGGGAAGCCCTGAGGATGACACTTGGCACAAAGCTGAGGAGACCCTAAGCCTCAGG   1100
GCGAACTTGGGGGTGGAAGACTTGGGGCTTTTCTAATCCTAAGGGGTCTGCGGTGGAAGAAAATGATTAGGCAGTTAAAGGCTAAACAGCCTTTTGTTTTCTTTTCAAATT   1200
CAGGGAACTGGGAGGTTTTCCCCGCTCCAAAAATGATTAGGAGAAAAAGGCTGAACACTTCCAACAGCCTTTTGTTTTCTTTTCAAATT   1300
TGGGGAAAGTCGGGAAACAGAGGCCTGCATTAAGAGGGTGGAACACATGGTCTCAGTCTCCAGTTCCAGTCTCCAGAGCCAGACATCCTGGGGTAGGTCC   1400
CCAGCCCTCCCAGTGCCCCTCCCGCTTGGTAAGGTGGGAGAATTGCAGCCTTCAGAGTTAGGGCCCTGACAGCTCTCCATAGGTGGAGGCCTCAGG   1500
CAGGCAGGATGCTGGGTGGG GTAGGCAAGAAAGGGCCCAGAGGCCGCATGGGAAAACTATCCTCCATGTGACCCCCTATGCCGCTTCACCCCC   1600
ACCTGACATCCCCACCAGAAGCAAAGCCTCATGGGCTGCACAGGAAGCAGAGACTTCGCATTGGCTGGGTACCC   1700
CACAGGTTCTGGGAGGGGACTTAGCGAGGTGACTCAG ------------ 360 NT ------------ TGC   2100
```

FROM FIG. 2C

TGCTTCTTCCACCTCTTCTCCAACCCTGCCTTCCCAGGGCTCTGGCATTTAGACAGCCCTGTCCTTATCTGTGACTCAGCCCCTCATTCAGTATTAACA  3300

AAATGAGAAGCAGCAAAACATGGTCTGTGCTGGGCCCCTTGGCTCACCTCCCTGACTGTCCTCACCCTGACTTCAGGCCCCACTGTTCAGATCCCA  3400

GGCTCCCTGCCCCATCTCAGACACCCTGTCCAGCCTGTCCGACAAATGGCCCTTGTCACTGTACACTGTAGAAAGCAAAAAGGCATATCTCTACC  3500

CCTTGATATGCCTGTACCTCACCAACCAGCCCCAAGCCTGTCTTCACCCATCACTGTCTACACAGCCCTCTCTCTCCTAACAGAATTCTATTCCTCT  3600

GAAAGTCTTCAGAAAACTGGACCTAGATAGTGCCATGTCTGGGGAGGAATATGGCACCAGGCAGTGGAAACAAGGACAGATCGGTGTTATCTCACATTT  3700

GATCAGAGAGCATGATCTCTCTTAACAGACCTGCCACCCTAATCAACGGGAGTGCTCACACAAGTGGGAGTCTGAGAGCTTAGCCCTATGCCCACCCTGG  3800

FIG. 2D

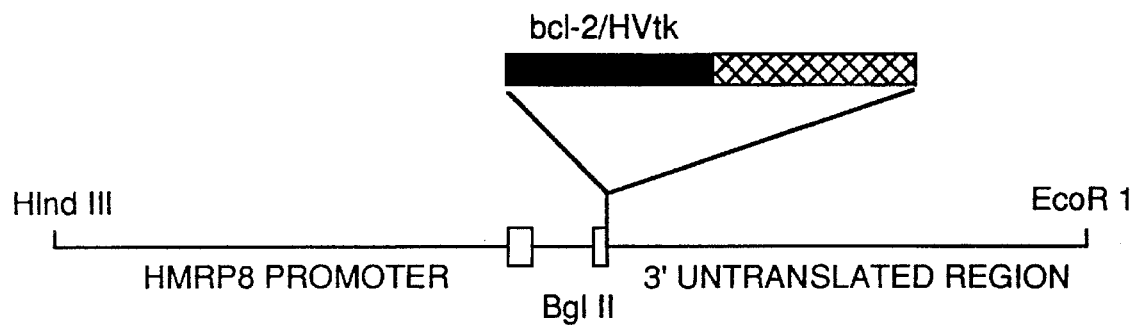
FIG. 7A
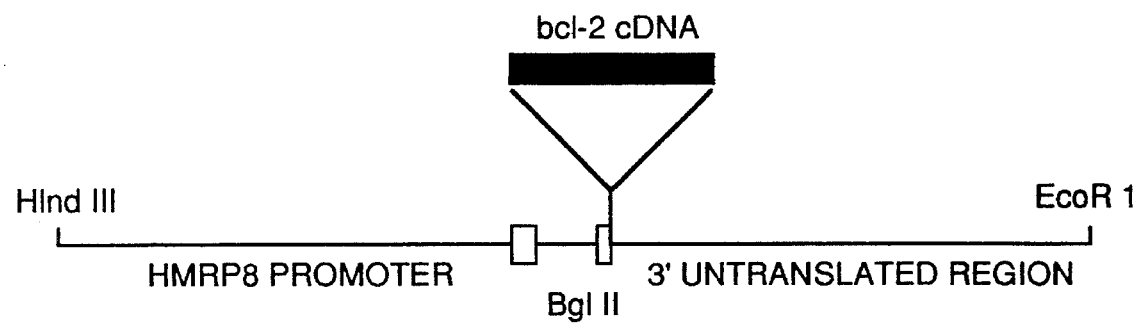
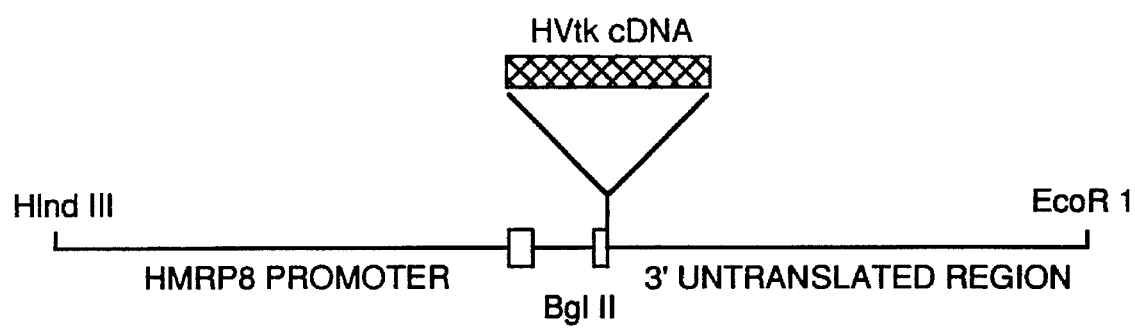
CO-TRANSFECTED CASSETTES
FIG. 7B

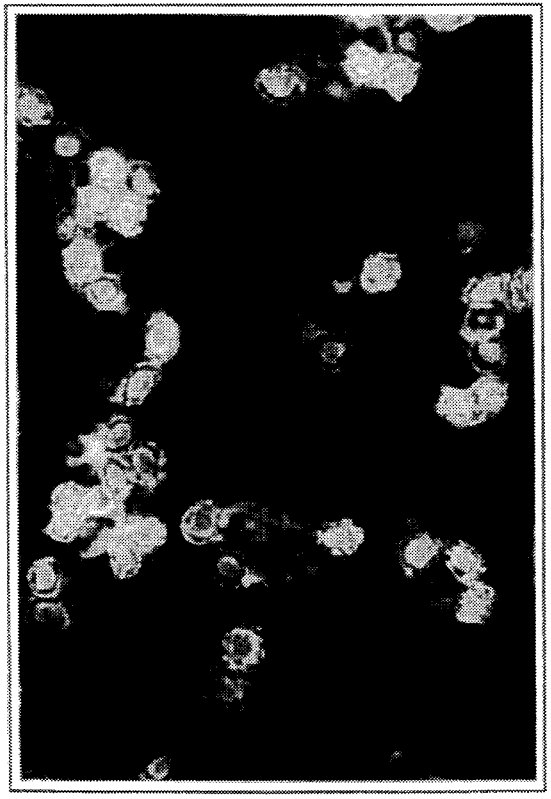 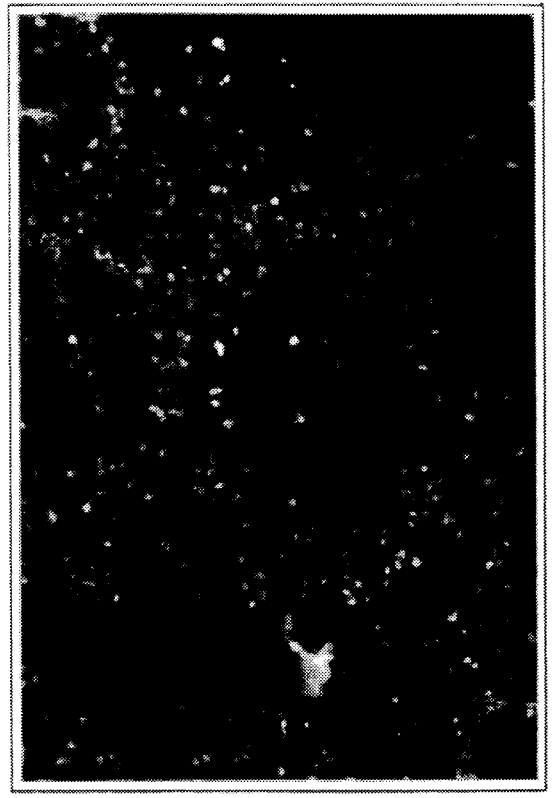
FIG. 8A  BONE MARROW    FIG. 8B  SPLEEN

METHOD AND COMPOSITIONS FOR MODULATING LIFESPAN OF HEMATOLYMPHOID CELLS

STATEMENT AS TO FEDERALLY SPONSORED RESEARCH

This invention was made with Government support under grant number CA42551 awarded by the National Cancer Institute. The Government has certain rights in this invention.

INTRODUCTION

1. Technical field

The invention relates to methods and compositions for producing mammalian hematopoietic stem cells in which the balance of cell death and cell proliferation of the transgenic cells and their progeny has been genetically altered. The invention can be used to treat diseases relating to deregulated or inopportune apoptosis.

2. Background of the Invention

In properly functioning tissues, the balance between cell death and cell proliferation is carefully regulated so that a remarkably invariant cell number is maintained. Loss of this tightly controlled balance may result in cancer, if cell proliferation dominates, or tissue degeneration, if cell loss dominates.

One of the ways in which balance is maintained is by apoptosis. This natural cellular process by which cells are programmed for death provides multicellular organisms with the molecular machinery to discard cells no longer needed such as during the developmental process and for homeostasis. As an example, apoptosis is observed in the immune system as the process by which B and T lymphocytes are removed when they fail to recognize a foreign antigen or when they are self-reactive. The proto-oncogene, bcl-2, is expressed in hematopoietic progenitor cells, including pre B cell lines which possess high levels of bcl-2 mRNA. Mature B cell lines express low levels of bcl-2, consistent with the programmed cell death associated with maturation and terminal differentiation of hematopoietic progeny cells. Cell killing by cytotoxic T cells in mammals is not prevented by bcl-2 expression.

The deregulation of programmed cell death may result in a disease state. Degenerative diseases which result from excessive cell death include degenerative neurological diseases, such as Alzheimer's disease and Parkinson's disease which are associated with the death of particular subsets of neurons. The inopportune death of T cells in AIDS may be associated with physiological cell death. Physiological cell death may also be associated with transplant rejection. Diseases due to increased cellular proliferation are also possible due to deregulation of the apoptotic mechanism and include autoimmune diseases in which self-reactive B and T cells are allowed to persist. The term "physiological cell death" is used here to describe cell death that occurs by a mechanism that exists in the mammal to kill its own cells and includes apoptosis and programmed death as synonymous terms.

An imbalance of the cell proliferation and cell degeneration processes also may lead to development of neoplasias in cells deregulated for the control of apoptosis. As a protective mechanism against cancer, tumor necrosis factor can trigger apoptosis in transformed host cells. An important example of the type of cancers which develop when cell proliferation exceeds the normal balance, is human follicular lymphoma. As with other malignancies where the development of neoplasia is related to an oncogene, follicular lymphoma is characterized by a chromosomal breakpoint. The rearrangement in follicular lymphoma is the most common chromosomal translocation in human lymphoid malignancies, the t(14;18)(q32;q21) translocation, which is known to inhibit programmed cell death in B cells. The bcl-2 gene is translocated and deregulated in follicular lymphoma.

There is currently a need to develop a method for modulating cell proliferation and cell death in diseases related to an imbalance in these processes or where the normal invocation of apoptosis leads to an inappropriate result, using the tools of genetic engineering and gene therapy in tissues specifically associated with the disease. Reprogramming of apoptosis can be used as a means for treating or curing diseases related to programmed cell death.

RELEVANT LITERATURE

The human proto-oncogene, bcl-2 is expressed in early myeloid cells of the bone marrow but is absent in polymorphonuclear neutrophils of the blood (Hockenbery, D. M. (1991), PNAS USA 88:6961; Delia, D. 1992 79:1291).

The cell death (apoptotic) pathway of the nematode, Caenorhabditis elegans, has been described, including engulfment and disposal of dead cells and degradation of the DNA late in the process (Ellis, (1986) Cell 44:817–829; Ellis, (1991) Genetics 129:9–94; Hengartner, M. O. (1992) Nature 356:494–499). Activating mutants of the gene, ced-9, fail to exhibit programmed cell death indicating that the product of ced-9 is a negative regulator of apoptosis in C. elegans.

Mutations that affect the expression of the C. elegans ced-9, ced-3 and ced-4 genes enhance the regulatory affects on apoptosis. ced-9 is essential for C. elegans development and apparently functions by protecting cells which normally live during development from programmed cell death (Horvitz H. R., PCT application WO 93/25683). bcl-2 is the mammalian homolog of ced-9 both functionally (Vaux D. L., et al., (1992) Science, 258:1955–1957) and structurally (Horvitz, H. R. and Hengartner, M., PCT application WO 93/25683).

Transgenic CFTR (–/–) homologous mutant mice have been developed independently by Snouwaert, et al. ((1992) Science 257:1083–1088) and Dorin, J. R. et al. ((1992) Nature 359:211–215). This CFTR (–/–) mouse model exhibits many of the important phenotypic characteristics of human cystic fibrosis and provides the only currently available animal model for this human disease.

The MRP8 and MRP14 genes from which the myelomonoctye specific promotors were isolated and characterized by Lagasse, E. and Clerc, R. G. ((1988) Mol. Cell. Biol. 8:2402–2410) and Lagasse, E. and Weissman, I. L. ((1992) Blood 79:1907).

A method for treating cystic fibrosis using retroviral-mediated gene therapy to provide the wild type CFTR gene to epithelial cells has been developed by Collins, F in U.S. Pat. No. 5,240,846.

SUMMARY OF THE INVENTION

A method of using modulation of apoptosis as a means of treating diseases related to deregulation of apoptosis or an inopportune invocation of apoptosis is provided. Also provided are expression cassettes, transgenic hematopoietic stem cells and progeny thereof for use in the method, and non-human transgenic mammals producing the transgenic hematopoietic stem cells. The transgenic hematopoietic stem cells contain one or more copies of an open reading frame of interest under the control of an enhancer and/or promoter region obtainable from a gene expressed in progeny of hematopoietic stem cells, particularly cells of the myeloid series. Where decreased proliferation is desired, optionally, the cell can be transformed or cotransformed with a negative regulatory gene or a gene encoding cytotoxic activity, optionally in the presence of an exogenous agent. Expression of the open reading frame(s) results in modulation of the balance between cell proliferation and cell death of progeny of the transgenic stem cells. The transgenic stem cells are obtained by the steps of introducing, in vivo or in vitro, one or more copies of a transcription or expression cassette into hematopoietic stem cells and growing the resulting transgenic cells to produce progeny cells having an altered phenotype. The invention finds use for example, in modulating apoptosis of the progeny cells as a means of treating or curing disorders related to rate of cell proliferation or cell death in progeny cells of non-transgenic hematopoietic stem cells of the host mammal. The transgenic non-human mammals and isolated transgenic cells find use, for example, for screening for treatment modalities which prevent or promote cell death.

BRIEF DESCRIPTION OF THE DRAWINGS

Figure 1B:
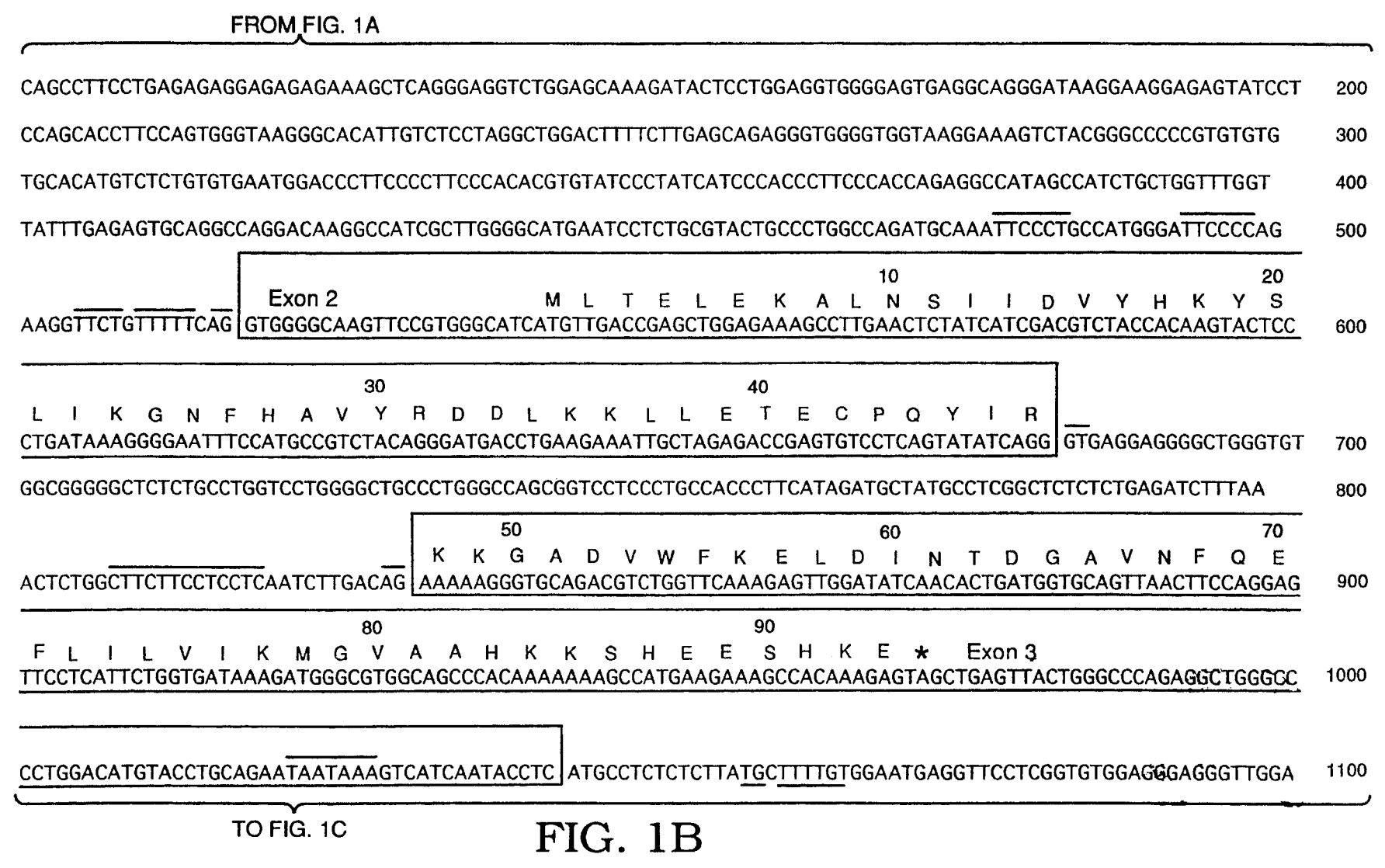

FIGS. 1A, 1B, 1C shows a diagrammatic representation of the human gene encoding MRP8 (SEQ ID NO: 1). The exon sequences are boxed, and the protein sequence (SEQ ID NOS: 2 and 3) is listed according to the one-letter amino acid code. Nucleotides are numbered according to the cap site (position +1). Conserved DNA motifs are overlined, and direct-indirect repeats are marked by arrows. The wavy line indicates a long Py-Pu stretch, and the dashed line splitting the 3' long inverted repeat indicates the AluI family repeated sequence.

FIGS. 2A, 2C, 2D shows a diagrammatic representation of the nucleotide sequence of the human gene encoding MRP14 (SEQ ID NO: 4). The exon sequences are boxed, and the protein sequence (SEQ ID NOS: 5 and 6) is listed according to the one-latter amino acid code. The codes are as described in the description of FIG. 1.

FIG. 7a shows a diagrammatic representation of the HMRP8/bcl-2/HVtk construct. Human bcl-2 cDNA (closed box) and HVtk are inserted in tandem in the BglII site between the second untranslated exon (open boxes) and the 3' untranslated region of the human MRP8 gene.

FIG. 7b shows a diagrammatic representation of the HMRP8/bcl-2 (described in FIG. 5) and the HVtk DNA construct for the expression of the HVtk from a separate construct for use in cotransfection with the HMRP8/bcl-2 construct. Human bcl-2 cDNA (closed box) and HVtk are inserted in tandem in the BglII site between the second untranslated exon (open boxes) and the 3' untranslated region of the human MRP8 gene.

FIG. 8 describes human bcl-2 expression in transgenic mice. (A) Bone marrow cells and (B) frozen sections of spleen were strained with anti-human bcl-2 mAb available from DAKO, Carpenteria, Calif. Control littermates demonstrated no reactivity (data not shown).

DESCRIPTION OF THE PREFERRED EMBODIMENTS

Figure 3:
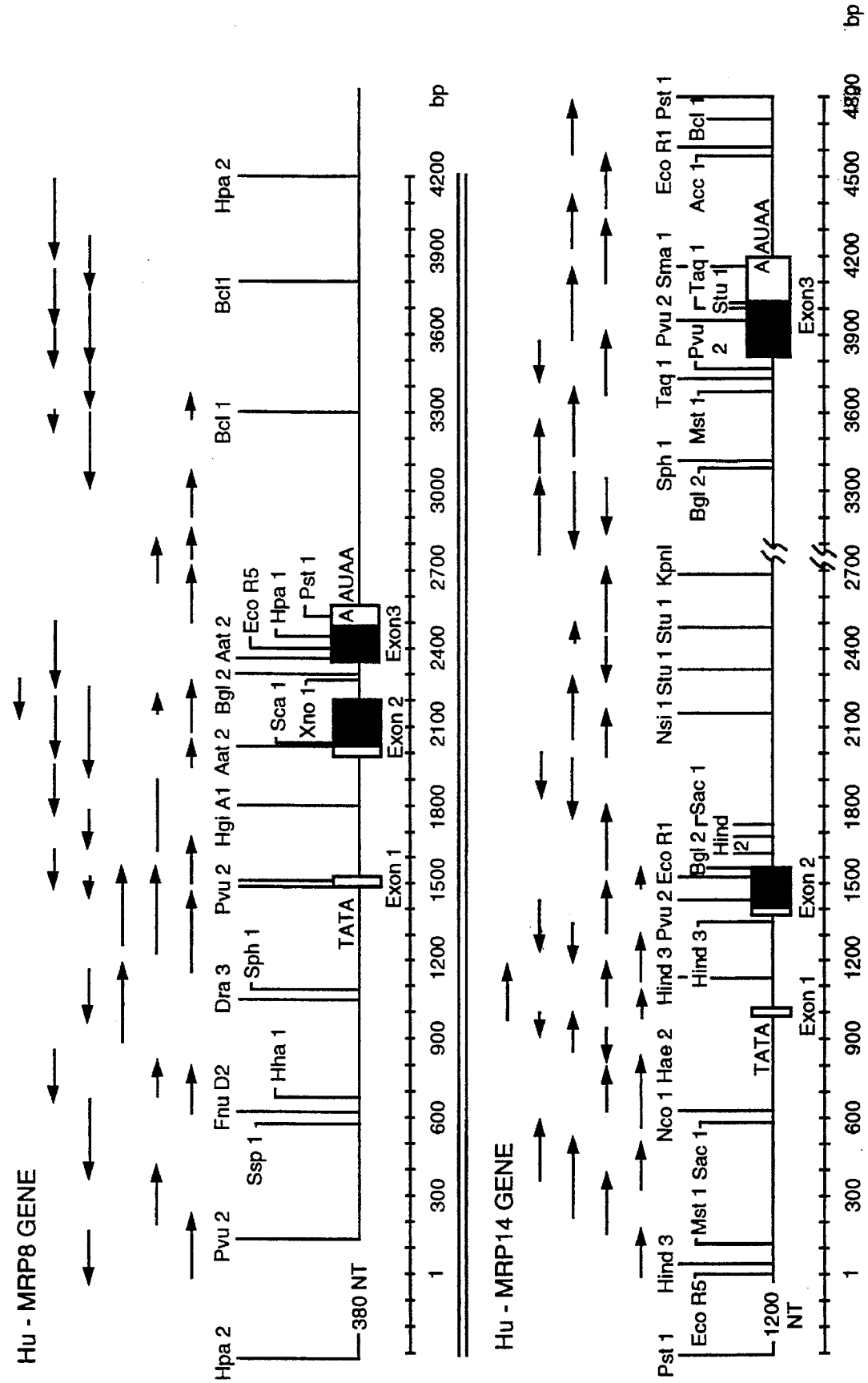
FIG. 3 shows a diagrammatic representation of the genomic organization and DNA-sequencing strategy of the human MRP8 and MRP14 genes. The black areas stand for the coding regions, and the boxed-in regions show the untranslated parts of the genes. The arrows point to the sequencing direction and end when the sequence is not clearly readable.
Figure 4:
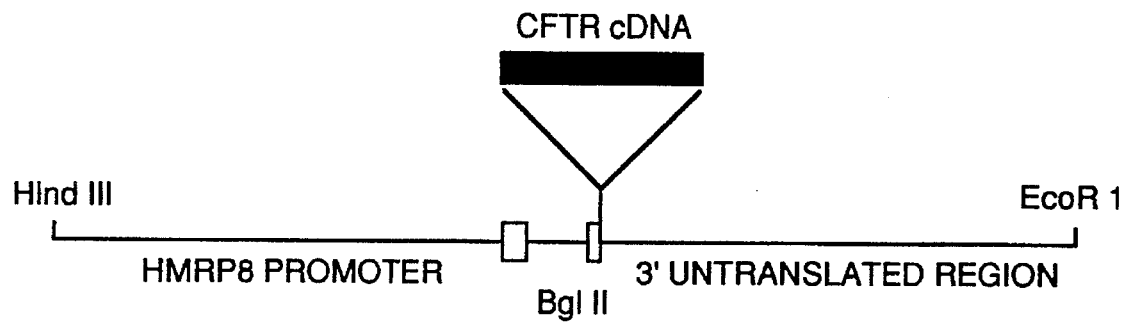
FIG. 4 shows a diagrammatic representation of the HMRP8/CFTR construct. Human CFTR cDNA (closed box) was inserted in the BglII site created by deleting from nucleotide position +536 to +1012 and inserting a BglII linker between the second untranslated exon (open boxes) and the 3' untranslated region of the human MRP8 gene. The approximately 8 kb HinDIII/EcoRI fragment was used for microinjection.

In accordance with the subject invention, methods of treating diseases of progeny cells of the hematopoietic system are provided together with compositions for use in the method. Stem cells can be transfected in vivo in a host mammal or they can be removed from a donor host, transfected in vitro and introduced into the donor host or a recipient host, preferably a human host. The invention is also directed to a transgenic non-human eukaryotic animal, preferably a rodent, such as a mouse, together with methods and compositions for preparing and using the transgenic animal. Nucleic acid constructs are provided which combine a transcriptional and optional translational expression region with an open reading frame of interest and a translational and/or transcriptional termination region. Generally the open reading frame encodes a first protein involved in cell proliferation or cell death. Optionally, cellular proliferation can be further regulated by the use of, on the same construct or on a separate construct, a gene which encodes a second protein the function of which antagonizes the action of the first protein, providing finer control of cell proliferation or cell death. An expression cassette contains the necessary sequences (promoter, open reading frame of interest and ribosome binding site) for transcription and translation of the transcribed mRNA into the protein of interest. For embodiments in which antisense mRNA is to be produced, an expression cassette contains all of the necessary sequences (promoter and open reading frame of interest but not a ribosome binding site) for the transcription of the open reading frame but not for its translation of mRNA into protein.

Diseases susceptible to treatment by the method of the subject invention include those caused by excessive cell death of non-transgenic hematopoietic cells in the host mammal due to viral infection such as HIV infection which ultimately causes AIDS and is characterized by the excessive dying of lymphatic T cells in the patient, and diseases related to excessive cell proliferation such as various cancers. The disease can be treated by providing transgenic hematopoietic stem cells which produce progeny cells in which the apoptotic pathway has been altered so as to decrease the rate of lymphatic T cell death.

Similarly, degenerative disorders such as cystic fibrosis (CF) also may be treated. CF is a fatal genetic disorder that affects about 1 of every 2500 newborns. The frequency of carriers is estimated to be about 5 percent. Abnormalities occur mainly in tissues and organs of predominantly epithelial cells, most notably in the lung. Symptoms of the disease include the appearance of granulocytes, particularly neutrophils, as an acute inflammation, and the release of nucleic acids from dying cells. It is a theory of the invention that the pathological changes in cystic fibrosis are mediated by the death of cells of the granulocyte series, followed by polymerization of their nucleic acids into sticky plugs that lead to infection and/or tissue damage in organs such as the lung. Cell death and the consequent release of nucleic acids to form viscous plugs in the lung may be associated with the excessive cell death of granulocytes. Thus, inhibition of granulocyte cell death is an important method by which the symptoms of the disease may be controlled. Providing the host mammal with transgenic stem cells that produce granulocytes in which the apoptotic pathway has been altered so as to decrease the rate of granulocyte cell death and alleviate the symptoms of the disease.

The subject invention offers several advantages over current treatment modalities for diseases related to cystic fibrosis. Current methods for treating the disorder focus on the treatment of epithelial cells of the affected tissue such as the lung. Recombinant viral vectors are used to introduce the wild type CFTR gene into the epithelial cells to reverse the genetic defect associated with the disease (Collins, F. S., 1993, U.S. Pat. No. 5240846). Current treatments do not address the control of cell death of hematolymphoid cells in the lung as a means of controlling the symptoms of cystic fibrosis caused by excessive cell death and release of nucleic acids to form the viscid mucous that is the principal cause of premature death.

Research into the nature of apoptosis in hematopoietic stem cells and their progeny has been seriously impeded by the lack of easily accessible animal models. Cystic fibrosis research, specifically, has been adversely affected due to the lack of animal models. Recently, animal models of CF were independently developed by Snouwaert, J. N. et al ((1992) Science 257:1083–1088) and Dorin, J. R. et al. ((1992) Nature 359:211–215) in which the CFTR gene is disrupted by using an insertional gene target vector in embryonic stem cells to produce the transgenic animal model displaying the symptoms of cystic fibrosis very closely modelling important features of cystic fibrosis in humans. However, this animal model does not address the need for an animal model in which cells of the myeloid and lymphoid series specifically are involved in the development of the disease. Transgenic animals have been developed which are Bcl-2-deficient (Veis, D. J. et al. (1993) Cell 75:229) or mutated (Nakayama, K. et al. Science 261:1684). However, no transgenic animal is currently available in which the wild type bcl-2 gene is expressed in hematopoietic stem cells and their progeny for the purpose of inhibiting apoptosis in the myeloid or lymphoid cells of interest.

For treatment of a disease relating to over or under proliferation of progeny cells of interest of a hematopoeitic stem cell, a nucleic acid construct which provides for modulation of apoptosis is introduced into the hemopoietic cells by any of a variety of different methods. The methods which can be used include "ex vivo" transfection of a target cell using either naked DNA, DNA-liposome conjugates or retroviral vectors followed by implantation of the transformed cells into the bone marrow of the host mammal, such as a mouse or a human. Progeny cells of interest include the cells of myeloid and lymphoid series, particularly the cells of the myeloid series and most particularly, the cells of the myelomonocytic series, especially neutrophils. The nucleic acid construct is introduced into host hematopoeitic stem cells either by direct introduction of the construct into the host mammal, or by in vitro transfection of stem cells taken from a donor mammal and introduction of the transfected cells back into the donor mammal or into an immunologically incompetent or immunologically compatible recipient host mammal. By immunologically incompetent is intended a host rendered incompetent by medical treatment, congenital incompetency, or acquired incompetency, as in AIDS. By immunologically compatible is intended a host that shares crucial histocompatibility genes. The transgenic stem cells can be grown on vitro or in vivo to produce transgenic progeny cells expressing an open reading frame of interest.

The nucleic acid construct to be introduced into a host mammal cells can include targeting constructs, transgenes, or open reading frames. The construct can be transferred to host cells by any suitable technique, including microinjection, electroporation, lipofection, biolistics, calcium phosphate precipitation, and viral-based vectors, among others. Other methods used to transform mammalian cells in vitro include the use of Polybrene, protoplast fusion, and others (see generally, Sambrook et al. Molecular Cloning: A Laboratory Manual, 2d ed., 1989, Cold Spring harbor Laboratory Press, Cold Spring Harbor, N.Y.). Mammalian cells also may be transfected in vivo using the method of introducing into the blood the nucleic acid complexed with a cationic lipid carrier. Approximately 70% of the bone marrow-derived cells, including primitive or blast cells stained for the marker gene product when transfected using a cationic lipid carrier in vivo (Debs, R. J., (1993) PCT patent application WO 93/24640). It is preferable to use a transfection technique with linearized transgenes containing only modified target gene sequence(s) and without vector sequences.

Screening techniques for determining the presence of the nucleic acid or protein of interest in the cell of interest are well known in the art. Brief descriptions of such techniques are described herein. Further description is obtained from Sambrook et al. (Molecular Cloning: A Laboratory Manual, 2d ed., 1989, Cold Spring Harbor Laboratory Press, Cold Spring Harbor, N.Y.).

For introducing a transgene which is to be nonhomologously integrated and form a transgenic nonhuman animal (e.g., mouse), pronuclear microinjection of fertilized eggs (e.g., mouse) is preferred. For making transgenic nonhuman animals which include homologously targeted nonhuman animals, embryonal stem cells (ES cells) are generally preferred. Murine ES cells, such as AB-1 line grown on mitotically inactive SNL76/7 cell feeder layers (McMahon and Bradley, Cell 62:1073–1085 (1990)) essentially as described (Robertson, E. J. (1987) in *Teratocarcinomas and Embryonic Stem Cells: A Practical Approach*. E. J. Robertson, ed. (Oxford:IRL Press), p. 71–112) may be used for homologous gene targeting. Other suitable ES lines include, the E14 line (Hooper et al. (1987) Nature 326:292–295), the D3 line (Doetschman et al. (1985) *J. Embryol Exp. Morph.* 87:27–45), and the CCE line (Robertson et al. (1986) Nature 323:445–448). The success of generating a mouse line from ES cells depends on the pluripotence of the ES cells (i.e., their ability, once injected into a host blastocyst, to participate in embryogenesis and contribute to the germ cells of the resulting animal). The blastocysts containing the injected ES cells are allowed to develop in the uteri of pseudopregnant nonhuman females. Resultant transgenic mice having a gene of interest that modulates the lifespan of cells operably linked to a hematolymphoid cell expressing gene regulatory sequence of interest such as MRP8 or MRP14 are screened for the presence of the correctly targeted construct and/or transgene(s) by PCR or Southern blot analysis on tail or other tissue biopsy DNA so as to identify transgenic mice having the gene of interest in the desired location(s). Such transgenic animals are useful sources of transgenic hematopoietic stem cells that express the gene of interest in specific progeny cells such as neutrophils. The transgenic hematopoietic stem cells are useful for transplantation and immunomodulatory drug screening assays.

Where the nucleic acid construct is an expression cassette, it includes as operably linked components in the 5'-3' direction of transcription, a transcriptional and translational initiation region associated with gene expression in hematopoietic stem cells and selected progeny cells, DNA encoding a product, expression of which results in an alteration of the balance between cell proliferation and cell death, and a transcriptional and translational termination region functional in the host cell. One or more introns may also be present.

Other components may be included in the expression cassette. For example, as appropriate DNA providing for secretion or insertion of the expression product into a cell membrane can be included in the expression cassette. Optionally, a second open reading frame capable of regulating the expression of the first open reading frame is present on the same construct or a different construct cotransformed for expression in the same cell. In some cases, an exogenous compound such as a substrate or effector of the product of the open reading frame is supplied exogenously to the host mammal to assist in achieving the desired physiological effect on cell proliferation.

Where homologous recombination is used to insert an open reading frame of interest into an endogenous gene locus expressed specifically in a target cell, the gene coding sequence in the construct is typically flanked upstream by a homology region that contains sequences homologous with the 5'untranslated region of the endogenous gene and flanked downstream by a sequence that occurs in the endogenous gene downstream of the transcription start site and containing the termination region. By this means, correctly targeted homologous integration positions the gene of interest so that it can be efficiently transcribed and translated into functional protein capable of modulating the lifespan of the cell. Where targeting constructs are used to transform hematopoietic stem cells, generally a selectable marker (e.g., neo or gpt) also is employed to provide a means for drug selection and identification of cells having homologously integrated targeting constructs. When selectable marker expression cassettes are included in a targeting construct, they are preferably positioned in a non-interfering location, such as between the down stream terminus (i.e., polyadenylation site) of the gene of interest and the downstream homology region.

The initiation region (also sometimes referred to as "promoter") is one which provides for expression in progeny of hematopoietic stem cells as compared to other progeny. The transcriptional initiation region may be endogenous to the host animal or foreign or exogenous to the host animal. By foreign is intended that the transcriptional initiation region is not found in the wild-type animal host into which the transcriptional initiation region is introduced. By endogenous, is intended sequences indigenous (i.e. natural to) the host animal as well as those not natural to the host animal but present as a result of an infectious disease, e.g. viral, and the like. By expression, is intended the transcription of an open reading frame to produce mRNA which can function as an antisense regulator of open reading frame expression if no translational start site including a ribosome binding site sequence is present for the translation of the mRNA. By expression, also is intended the transcription of an open reading frame to produce mRNA which can be translated into the protein of interest if a functional translational start site including a ribosome binding site is encoded in the sequence.

The promoter preferably comprises a transcriptional initiation regulatory region and translational initiation regulatory region of untranslated 5' sequences, "ribosome binding sites," responsible for binding mRNA to ribosomes and translational initiation. The transcriptional initiation regulatory region may be composed of cis-acting subdomains which activate or repress transcription in response to binding of trans acting factors present in varying amounts in different cells.

It is preferred that all of the transcriptional and translational functional elements of the initiation control region are derived from or obtainable from the same gene. In some embodiments, expression will be modified by the addition of sequences, such as enhancers or negative regulators or deletions of non-essential and/or undesired sequences. By "obtainable" is intended a promoter having a DNA sequence sufficiently similar to that of a native promoter to provide for the desired specificity of transcription of a DNA sequence of interest. It includes natural and synthetic sequences as well as sequences which may be a combination of synthetic and natural sequences.

The promoter preferably is one which provides for preferential expression, or at least substantially specific expression, in progeny cells of interest of hematopoietic stem cells.

By substantially specific expression, is intended expression in a cell type of interest and low (less than 10%, preferably less than 1% of that in the cell type of interest) or undetectable expression in other cell types. The promoter, with or without an enhancer region (see below) must function in the host cells of interest. Preferred promoter and/or enhancer regions are those obtainable from genes expressed in the cells of the myelomonocytic series. Of particular interest as a transcriptional initiation region which is preferentially expressed in granulocytes, is one from a gene which is functional in the myelomonocytic cell series of the host mammal. Examples of such regions include those obtainable from the MRP8 and MRP14 genes and which are expressed in cells of the myelomonocytic series, especially neutrophils but not in macrophages.

Any mammalian cells can serve as a source for a promoter of interest. Human cells are preferred as a source for nucleic acid for preparing the desired sequences for use in humans. To identify promoters having the desired characteristics of cell type specific expression, differential screening techniques are used. For example, promoter-probe and terminator-probe plasmid vectors are constructed to facilitate the isolation and characterization of regulatory DNA sequences in vivo. The vectors use the principle of "insertional activation" of a transcriptionally silent vector-encoded marker gene made transcriptionally silent by deleting its promoter and leaving in its place a unique restriction enzyme cleavage site. Recombination of the vector into the genome of the cell type of interest provides the chance that the marker gene will recombine into a transcriptionally active site in the proper orientation for expression of the marker gene. Preferential expression of the marker in the cell type of interest relative to other cell types indicates that the site of insertion is near a cell type specific promoter. Isolation of the DNA upstream of the marker gene and including the cell type specific promoter is performed by fragmentmenting DNA, subcloning into a vector, isolating populations of genomic DNA fragments that hybridize to a probe complementary to the marker gene, sequencing the positive subclones, and analyzing the upstream genomic region for consensus promotor sequences. (See generally: Rodriguez, R. L. and Tait R. C., 1983, Recombinant DNA Techniques: An introduction, Sambrook, 1989, Molecular Cloning, CSH)

Hematopoietic stem cell progeny-specific transcription suggests that gene regulatory proteins may be bound to enhancer sequences and other upstream promoter elements. By enhancer element (enhancer) is intended a regulatory DNA sequence that is capable of activating transcription from a promoter linked to it with synthesis beginning at the normal RNA start site which is capable of operating in both orientations (normal or flipped); and which is capable of functioning even when moved either upstream or downstream from the promoter. Both enhancers and other upstream promoter elements bind sequence specific DNA-binding proteins that mediate their effects. As an example, for the MRP8 or MRP14 genes, to identify the exact nucleotide sequences important for the function of the enhancer(s), and other upstream elements, fragments of the MRP8 or MRP14 protein untranslated 5'-region of the gene which is the source of the promoter is screened for its capacity to modify the function of an endogenous or heterologous promoter.

The activity of each enhancer and other upstream promoter elements generally is present on a segment of DNA which may contain binding sites for multiple proteins. The binding sites can generally be dissected by preparing smaller mutated versions of the enhancer sequence joined to a reporter gene whose product is easily measured. The effect of each mutation on transcription can then be tested. Alternatively, fragments of this region can be prepared. Each of the mutated versions of the enhancer sequence or the fragments can be introduced into an appropriate host cell and the efficiency of the expression of the reporter gene measured. Those nucleotides required for enhancer function in this test are then identified as binding sites for specific proteins by means of gel mobility shift and DNA footprinting studies.

An alternate means of examining the capability of isolated fragments of the region upstream of the promoter to enhance expression of the reporter gene is to look for subdomains of the upstream region that are able to enhance expression of levels from a test promoter which comprises the TATA CAAT box but shows little or no detectable activity. A fragment of the 5'-region is inserted in front of the test promoter in an expression cassette, and the effect on expression of the reporter gene evaluated.

A promoter from a gene expressed in hematopoietic stem cell progeny in tissue of the host animal may be employed for varying the phenotype of the host animal. The transcriptional level should be sufficient to provide an amount of RNA capable of resulting in a modified animal. By "modified animal" within the subject invention is meant an animal having a detectably different phenotype from a nontransformed animal of the same species, for example one not having the expression cassette, including the open reading from of interest in its genome. Various changes in phenotype are of interest. These changes include modified cell death or cell proliferation of cells of the myelomonocytic series, expression of the open reading frame of interest in bone marrow, spleen and blood, limited to myeloid and neutrophil cells and not in tissue macrophages.

Examples of open reading frames of interest for expression in the myelomonocytic cell series include a coding sequence from the CFTR gene; a bcl-2 gene, preferably obtainable from a human or a mouse; a herpesvirus thymidine kinase gene; a fas-FKBP fusion protein; genes encoding granule proteins (e.g, lactoferrin, vitamin-B-12-binding protein, defensin, and gelatinase); myeloperoxidase (MPO); oncogenes (e.g., c-myc, rxr and pml/rar$\alpha$); $\alpha$-1-antitrypsin, deficient in hereditary emphysema; and genes associated with Chronic Granulomatous Disorder (CGD) (e.g., gp91-phox, p22-phox, p47-phox or p67-phox) as well as other genes which have the capacity to alter the lifespan of a cell. By coding sequence is intended the natural sequence obtainable from the gene, as well as coding sequences from mutant genes, sequences of less than the full coding sequence of the gene and antisense sequences, with the proviso that expression of the open reading frame directly or indirectly alters apoptosis in the cells expressing the coding sequence. The activity of the expression product of the coding sequence may be more or less than that of the natural expression product. In the case of antisense sequences, the sequence may be from about 12 nucleotides, preferably about 24 nucleotides, up to the full length of the corresponding sense strand.

The presence of the open reading frame of interest in transfected cells is ascertained by screening techniques well known to those skilled in the art, such as immunohistochemical staining using an antibody specific for the product of the open reading frame of interest as well as Southern analysis or functional assays for the protein of interest. The expression of antisense mRNA from an open reading frame of interest may be ascertained by techniques well known to those skilled in the art, such as Northern analysis using a probe complementary to the sequence of interest.

The termination region is native with the transcriptional initiation region, or is native with the DNA sequence of interest, or is derived from another source. Examples of termination regions which find use in the subject invention include the 3' termination region of the MRP8 or MRP14 genes as well as the SV40 viral termination region, well known in the art for use in termination or any other termination known to those of skill in the art which will function in the host cells of interest.

Nucleotide sequences of the constructs are linked together in conventional 5'-3' linear polynucleotide linkage. Construction of a vector for use in the instant invention includes assembling the sequence of the MRP8 or other promoter which is expressed in a hematopoietic cell type of interest, a coding region a bcl-2 sequence or another open reading frame of interest and transcriptional and translational termination sequences so that the components are operably joined for expression of the reading frame of interest in hematopoietic cells, either isolated cells in culture or in a host mammal. Using molecular genetic techniques well known in the art, the open reading frame of interest is inserted between the promoter and/or enhancer region and the termination sequences at a unique restriction site or sites such that the coding sequence is translated in-frame.

In a preferred embodiment, the nuclieic acid construct is an expression cassette which includes a human bcl-2 gene coding sequence under the regulatory control of a promoter from a gene expressed in the myeloid cell series, preferably an enhancer and/or promoter from a MRP8 or MRP14 gene, both of which function in cells of the myelomonocytic series. Negative regulation of the expressed gene may optionally be obtained by the concurrent expression of a gene that negatively regulates the primary agent controlling cell death and cell proliferation. In the case of bcl-2 expression, the preferable negative regulator is the herpesvirus thymidine kinase (HVtk) gene, or optionally, the fas-FKBP fusion cassette. Administration of a substrate of thymidine kinase, such as gancyclovir, which is enzymatically converted to a cytotoxic product, to a host producing cells expressing HVtk results in death of those cells due to the cytotoxicity of the metabolic product obtained by action of the thymidine kinase on the substrate.

The fas gene product, Fas, is a membrane receptor that induces apoptosis most likely through a mechanism separate from bcl-2 regulation (Itoh, N. et al., (1993) J. Immunol. 151:621–627). Pairing of membrane receptors for enhancement of signalling effects has been shown for the Ig receptor complex protein MB-1/Igα, for example, through the use of an FKBP (FK binding protein)-receptor fusion product to dimerized when bound to the dimer ligand, FK1012 (Spencer, D. M., et al. (1993) 262:1019–1024). Enhanced induction of apoptosis by fas-FKBP pairing in the presence of FK1012 is a useful embodiment of the subject invention as it allows for the killing of cells under circumstances where removal of transgenic cells is necessary.

Another preferred embodiment is a nucleic acid construct which includes the CFTR gene under the transcriptional and translational control of the endogenous CFTR promoter or under the control of the enhancer and/or promoter region of the MRP8 or MRP14 genes such that expression of the CFTR gene occurs in the hematopoietic progeny cells of interest, preferably in cells of the myelomonocytic series.

The presence of the expression cassette integrated into the genomic DNA can be identified by using carefully chosen primers and PCR or by Southern blot analysis, followed by analysis to detect if PCR products or Southern blot bands specific to the desired sequence are present. Several studies have already used PCR to successfully identify the desired transfected cell lines (Zimmer and Gruss (1989) Nature 338:150; Mouellic et al. (1990) PNAS 87:4712; Shesely et al. 1991 PNAS 88:4292). This approach is very effective when the number of cells receiving exogenous targeting construct(s) is high (i.e., with electroporation or with liposomes) and the treated cell populations are allowed to expand (Capecchi, M. (1989)).

The transgenic animal expresses a gene involved in the balance of cell death and cell proliferation, preferably the human bcl-2 gene sequence at a level in hematopoietic stem cells and their progeny cells of interest under the transcriptional and translational control of a promoter and/or enhancer region that functions in the cells of interest, preferably the promotor/enhancer region of the MRP8 and MRP14 genes with expression occurring preferably in the cells of the myelomonocytic series such that the cells of interest are altered in their ability to modulate cell death or cell proliferation. In the case of cells of the myelomonocytic series where the disease is related to increased cell death, the preferable embodiment provides that the cells of interest are inhibited from progressing through the process of apoptosis, preventing early death of these cells in the tissue of interest. Apoptotic cell death displays marked plasma membrane blebbing, volume contraction, nuclear condensation and the activation of a $Ca^{2+}/Mg^{2+}$ dependent endonuclease that cleaves DNA into nucleosomal length fragments.

Preferably, human bcl-2 expression is limited to myeloid monocyte and neutrophil cells with expression observed in the red pulp and marginal zone of spleen consistent with the expression pattern for MRP8. Preferably, peritoneal and bone marrow macrophages are negative for transgenic bcl-2 expression. The expression of bcl-2 under the transcriptional and translational control of the MRP8 promoter/enhancer region has no affect on the clearance of transgenic neutrophils by phagocytosis avoiding the buildup of transgenic cells due to reduced cell death. The expression of coding sequence from a bcl-2 gene or other gene of interest, expression of which modulates the lifespan of a hematolymphoid cell of interest may be determined by immunohistochemical techniques well known in the art using an antibody to the gene product of interest or a nucleic acid probe if the gene product of interest is antisense RNA.

Treatment of disorders caused by adverse changes in the balance between cell proliferation and cell death is performed in mammals, especially humans, by the method in which transgenic hematopoietic stem cells are returned from in vitro culture into the bone marrow of the host animal made immunoincompetent by X-irradiation where the transgenic cells become incorporated into the animal and can give rise to cells of the hematolymphoid series, including granulocytes, and particularly neutrophils. Bone marrow transplantation from HMRP8/bcl-2 transgenic mice into CFTR (–/–) mice (Snouweart, 1992, op. cit.) is provided as an embodiment of the subject invention as a treatment for the loss or mutation of the CFTR gene associated with CF in humans. Treatment by HMRP8/bcl-2 hematopoietic stem cells transplanted into transgenic CFTR knockout mice as animal models of CF is evaluated by the observation of the full or partial reversal of the CFTR knockout phenotype including early death generally between 30 and 50 days after birth, failure to thrive, neconium ileus, alteration of mucous and serous glands, and obstruction of glandlike structures with inspissated eosinophilic material.

The cystic fibrosis disorder is correlated with the appearance of a defective CFTR gene whose product is a membrane protein that can act as a chloride channel. The CFTR gene is expressed in epithelial cells as well as blood cells, and may be expressed in granulocytes. Two proteins that are cystic fibrosis-associated, MRP8 and MRP14, are cytoplasmic calcium-binding proteins of cells of the myelomonocytic series, including granulocytes. Expression from the promoter/enhancer region of the HMRP8 and HMRP14 genes occurs in early myeloid cells to blood neutrophils and monocytes but not in tissue macrophages (Lagasse 1992, Blood 79:1907). The appearance of the MRP8 and MRP14 proteins in secretions and body fluids of cystic fibrosis patients are likely to be derived from their release from dying granulocytes. Transplantation of humans with hematopoietic stem cells carrying the wild type CFTR gene or transplantation of humans with transgenic human hematopoietic stem cells carrying the CFTR gene, the bcl-2 gene, the HVtk gene and other genes of interest is a treatment for disorders that are reversed by the modulation of the lifespan of hematolymphoid cells, particularly neutrophils.

The neutrophils of the HMRP8/bcl-2 transgenic mouse may be used for in vitro screening of compounds to find inhibitors of inflammatory mediators expressed by the transgenic hematolymphoid cells.

An embodiment of the subject invention provides a transgenic mouse expressing viral thymidine kinase in hematolymphoid cells, such as myelomonocytic cells, under the transcriptional and translational control of a cell type specific promoter such as the human MRP8 or MRP14 promoter. This transgenic animal is useful as a model of gene therapy control systems as well as a model for a treatment system for the reduction of neutrophil recruitment in the treatment of CF. Where the recipient host mammal is immunoincompetent, the source of the cells may be from an unrelated donor mammal, including a donor mammal of a different species. Of particular interest is the introduction of transgenic human hematopoietic stem cells into an immunocompromised non-human mammal, such as a mouse, as a means of screening for the effects of various treatment protocols on the transgenic human progeny cells. An example of a host mammal is a SCID/hu mouse.

An embodiment of the subject invention provides for the control of cell death in gene therapy as a means of providing treatment against excess proliferation of the transgenic cells as well as a means of providing safety in gene therapy to remove transgenic cells that become pathological during treatment. The embodiment provides the inclusion in the expression cassette comprising the open reading frame of interest, such as bcl-2, at least one and preferably both of the genes encoding HVtk and fas-FKBP. The treatment of a HMRP8/HVtk transgenic animal such as a mouse or, preferably, a human with a calibrated dose of a substrate for thymidine kinase, such as gancyclovir or a similar compound kills the dividing transgenic cells. Gancyclovir is commercially available from Syntex (Palo Alto, CA) and information regarding its administration to animals, including humans, is available in various sources in the art, including human prescribing directions from package inserts. Treatment of a fas-FKBP transgenic animal such as a mouse or, preferably, a human with a calibrated dose of the fas-FKBP inducer, FK1012 or similar compound, induces apoptosis in the transgenic cells expressing fas-FKBP in a cell type specific fashion. Treatment with both gancyclovir and FK1012 provides for substantially complete killing of the transgenic cells. By substatially complete killing is intended the absence of pathology or other effect due to the presence of the transgenic cells administered in gene therapy after killing by gancyclovir and/or FK1012. These embodiments using cell killing systems such as HVtk+gancyclovir and fas-FKBP+FK1012 provide a means of controlling neutrophil recruitment to the lung in CF; down-regulation of increased cell proliferation of transgenic cells; and when provided together on the same cassette with the open reading frame of interest they provide a safety system for the removal of pathogenic transgenic cells that can appear in gene therapy.

An embodiment of the subject invention provides for the use of the HVtk+gancylovir and fas-FKBP+FK1012 cell killing systems contained on seperate expression cassettes or, preferably, on the same cassette under the transcriptional and translational control of a cell type specific promotor such as MRP8 or MRP14 for the transfection, preferably in vivo, of mutant mammalian hematopoietic stem cells, preferably mouse, most preferably human cells for treatment of disorders caused by excess cell proliferation of hematolymphoid cells such as malignancy or autoimmune disorders.

An embodiment of the subject invention also provides a transgenic mouse expressing endogenous or supra-endogenous levels of wild type CFTR gene in hematolymphoid cells in which the MRP8 or MRP14 promoter is functional.

An embodiment of the subject invention also provides a transgenic mouse expressing supra-endogenous levels of bcl-2 in hematolymphoid cells in which the MRP8 or MRP14 promoter is functional as an animal model of human neutrophil neoplasia. The animals of the invention can be used as test animals for materials thought to confer antagonism to neoplasia associated with supra-endogenous expression of bcl-2 in hematolymphoid cell. An animal is treated with the material, and reduced proliferation of the isolated hematolymphoid cells of interest compared to untreated animals, is detected as an indication of protection.

The animals of the invention can be used to test a material as to its affects on acute inflammation by exposing the animal to the material and determining neutrophil behavior and rejection by macrophages.

Other features and advantages of the invention will be apparent from the description of the preferred embodiments, and from the claims. The following examples are offered by way of illustration and not by way of limitation.

EXAMPLES

Example I. Cloning of mouse MRP8 and MRP14 genes and construction of an expression cassette containing the human bcl-2 gene.

A human fetal liver DNA library established in the λ Charon 4A bacteriophage vector (Lawn et al, 1978) was screened by plaque hybridization. With the MRP8 cDNA probe (ref Odink, 1987), six positively hybridizing clones were identified from $6 \times 10^5$ independent phage plaques. Southern blot analysis of the purified DNA from clones AMRP8-1 to −6 showed that all six recombinant phage contained the complete MRP8 gene. A 5-kb HpaII DNA fragment encompassing the MRP8 gene was subcloned from phage λMRP8-3 into pBR322 linearized with ClaI (pBRMRP8). A HindIII-EcoRI fragment containing the MRP8 gene was similarly subcloned in HindIII-EcoRI-cut pUC8 (pUCMRP8). With the MRP14 cDNA probe, four positive phage plaques were identified and plaque purified. One clone kMRP14-2 containing the complete MRP14 gene on a 6-kb PstI DNA fragment was subcloned into the PstI site of pUC9 (pUCMRP14). The strategy used for sequencing the MRP8 and MRP14 genes in a plasmid subclone is depicted in FIG. 3; arrows indicate the direction of DNA sequencing. DNA sequencing was performed on bacteriophage M13 single-stranded templates according to the protocol of the manufacturer (Amerhsam). Construction of the HMRPS/bcl-2 expression cassette was performed using standard molecular biology techniques. Human bcl-2 cDNA (closed box) is obtained by synthesizing a pair of complementary PCR primers bracketing the bcl-2 gene coding sequence having BglII compatible ends and amplifying the region of expressed mRNA between the primers to produce the cDNA. The bcl-2 cDNA was inserted in the BglII (position 791) site between the second untranslated exon (open boxes) and the 3' untranslated region of the human MRP8 gene such that bcl-2 expression is in frame. The 4.5 kb HinDIII/EcoRI fragment was used for microinjection (Lagasse, E. et al., (1988) Mol. Cell Biol. 2402; and J. Exp. Med., (1994) in press).

Example II. Preparation of transgenic mice

HMRP8/bcl-2 transgenic mouse:

The HMRP8/bcl-2 construct was microinjected into fertilized mouse oocytes of the (C3H X B/J) F1 background and transferred to pseudopregnant recipients according to described techniques in Hogan, et al., *Manipulating the Mouse Embryo: A Laboratory manual,* Cold Spring harbor Laboratory (1988). Transgenic animals were obtained which harbored integrated copies of the bcl-2 construct, and the transgenic cells were further characterized as described in Example III. The transgenic hematopoietic stem cells of the HMRP8/bcl-2 mouse are useful in the treatment of the cystic fibrosis-like phenotype in a CFTR (–/–) mouse, the only animal model currently available that closely mimics the characteristic of human cystic fibrosis.

HMRP8/HVtk transgenic mouse:

The HMRP8/HVtk construct was microinjected into fertilized mouse oocytes of the (C3H X B/J) F1 background and transferred to pseudopregnant recipients according to described techniques in Hogan, et al., *Manipulating the Mouse Embryo: A Laboratory manual,* Cold Spring harbor Laboratory (1988). Transgenic animals are obtained which harbored integrated copies of the MRP8/HVtk construct, and the transgenic cells are further characterized.

HVtk-expressing cells are killed after administration of gancyclovir, an anti-herpesvirus agent nucleoside analog which is phosphorylated by HVtk but not by human thymidine kinase. Following synthesis of gancyclovir monophosphate (gancyclo-GMP) in HVtk-expressing cells, normal cellular enzymes catalyze the sequential synthesis of gancyclo-GDP and gancyclo-GTP. Gancyclo-GTP functions as an inhibitor of DNA polymerase and upon incorporation into DNA, causes chain termination. Gancyclovir has a low human toxicity due to its specificity as a substrate for HVtk.

The transgenic hematopoietic stem cells of the HMRP8/HVtk mouse are useful in the treatment of the cystic fibrosis-like phenotype in a CFTR (–/–) mouse, the only animal model currently available that closely mimics the characteristic of human cystic fibrosis, by allowing the death in the bone marrow of expressing and dividing neutrophil precursors in the presence of calibrated amounts of gancyclovir, reducing the number of neutrophils that may populate the lung where their death release DNA causing the viscous plug. The transgenic hematopoietic stem cells of the HMRP8/HVtk mice are useful in the treatment of the cystic fibrosis-like phenotype in a CFTR (–/–) mouse, the only animal model currently available that closely mimics the characteristics of human cystic fibrosis.

Example III. Bcl-2 Lengthens the Lifespan of Neutrophils But Not Their Engulfment by Macrophages.

Transgenic neutrophils of the mouse expressing human bcl-2 under the control of the MRP8 promoter/enhancer region were monitored for the affect of human bcl-2 expression on the lifespan of neutrophils in vitro.

Tissue were isolated from transgenic and littermate controls and treated as frozen sections. Serial sections were fixed in acetone at –20° C. for 5 min. Single-cell suspensions collected from peritoneal fluid, blood or bone marrow were cytospun and fixed as described above before immunohistochemistry.

Mouse neutrophils were isolated from the peritoneal cavity of bcl-2 transgenic and control mice by induction of an inflammation with 2 ml of a 3% thioglycolate medium (Difco, Detroit, MI). Peritoneal exudate cells were harvested 4 hours later by peritoneal lavage with PBS solution containing 5 mM EDTA. Peritoneal cells were counted and incubated in a 250 ml flask. Non adherent cells transferred after 2 hours to separate neutrophils from adherent peritoneal macrophages. The neutrophils were cultured in RPMI 1640 containing 10% heat-inactivated FCS and 100 U/ml penicillin, 100 mg/ml streptomycin.

Mouse peritoneal macrophages were isolated after induction of an inflammation in C57Bl/6 as described previously. Peritoneal exudate cells were harvested 4 days later by peritoneal lavage with PBS solution containing 5 mM EDTA. Peritoneal cells were plated in 24-well plates at $1 \times 10^6$ cells/well, and non adherent cells washed after 2 hours. The macrophage monolayers were cultured overnight in RPMI 1640 containing 10% heat-inactivated FCS and 100 U/ml penicillin, 100 mg/ml streptomycin.

For fluorescence-activated flow cytometry analysis single cell suspensions were stained with appropriate antibodies, and analyzed by FACScan® (Becton Dickinson & Co., Mountain View, CA). Cells were resuspended in staining medium (phosphate-buffered saline supplemented with 2% of fetal calf serum) containing propidium iodide (PI)(5 ug/ml). More than 10,000 cells were analyzed per sample. Dead cells stained with PI were grated out at the time of analysis.

The phagocytic assay was prepared as follows. Neutrophils and macrophages were isolated during thioglycolate-induced inflammation. Freshly isolated neutrophils or neutrophils aged in culture (16 mice total, $5 \times 10^6$ neutrophils per mouse) were resuspended in 1 ml of medium and then added to each washed cell of peritoneal macrophages ($10^6$ macrophages per well for a 24 wells plate cultured for two days). The macrophage monolayers were a mixture from two to three different C57Bl/6 donors. After 30 min. incubation at 37° C. in a 5% $CO_2$ atmosphere, the wells were vigorously washed with cold (4° C.) PBS, fixed with 2% formaldehyde in PBS, and then stained for myeloperoxidase by the method of Newman et al ((1982) J. Exp. Med. 156:430). Macrophages were scored as positive if they contained one or more myeloperoxidase-positive neutrophils.

Figure 5:
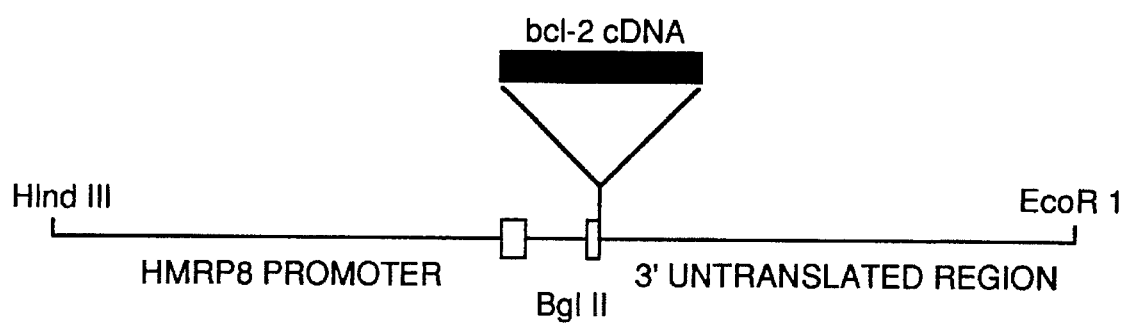
FIG. 5 shows a diagrammatic representation of the HMRP8/bcl-2 construct. Human bcl-2 cDNA (closed box) was inserted in the BglII site between the second untranslated exon (open boxes) and the 3' untranslated region of the human MRP8 gene. The approximately 4.5 kb HinDIII/EcoRI fragment was used for microinjection.
Figure 6:
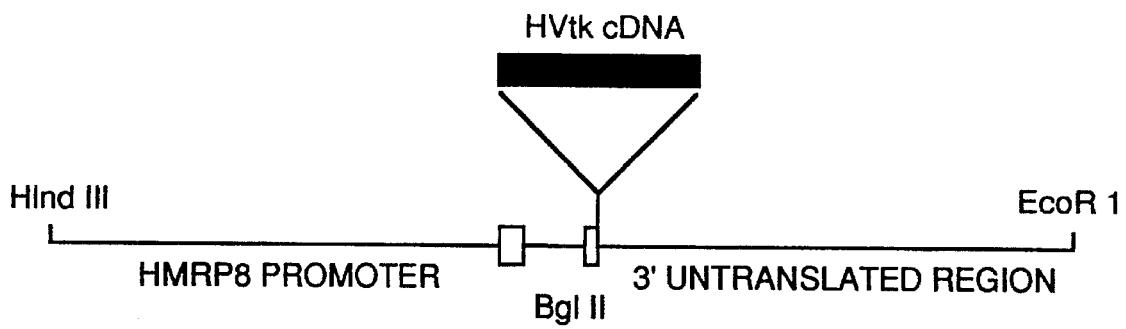
FIG. 6 shows a diagrammatic representation of the HMRP8/HVtk construct. Herpesvirus thymidine kinase (HVtk) DNA (closed box) is inserted in the BglII site between the second untranslated exon (open boxes) and the 3' untranslated region of the human MRP8 gene. The 4.5 kb HinDIII/EcoRI fragment is used for microinjection.

The transgene was constructed by inserting human bcl-2 cDNA under the control of the human MRP8 regulatory regions as shown in FIG. 5 (Lagasse, E. (1988) MCB 8:2402). Four lines of transgenic mice were established. Only one line was used extensively for this study and the others, which have the same phenotype, were reserved for verification of key findings. Tissue-specific expression of the transgenic bcl-2 was examined by immunohistochemistry. Human bclo2 expression was present in bone marrow, spleen (FIG. 8) and blood (not shown). The MRP8 gene is known to be strongly expressed in stages of early myeloid cells to blood neutrophils and monocytes, but not in tissue macrophages (Lagasse, E. and Weissman, I. L. 1992. Blood 79:1907). Analysis of bone marrow and blood cells confirmed that human bcl-2 expression was limited to myeloid and neutrophil cells. In spleen, only the red pulp and marginal zone were positive, consistent with the expression pattern described for MRP8 and other myeloid markers. Peritoneal and bone marrow macrophages were always negative for transgenic bcl-2.

Figure 9A:
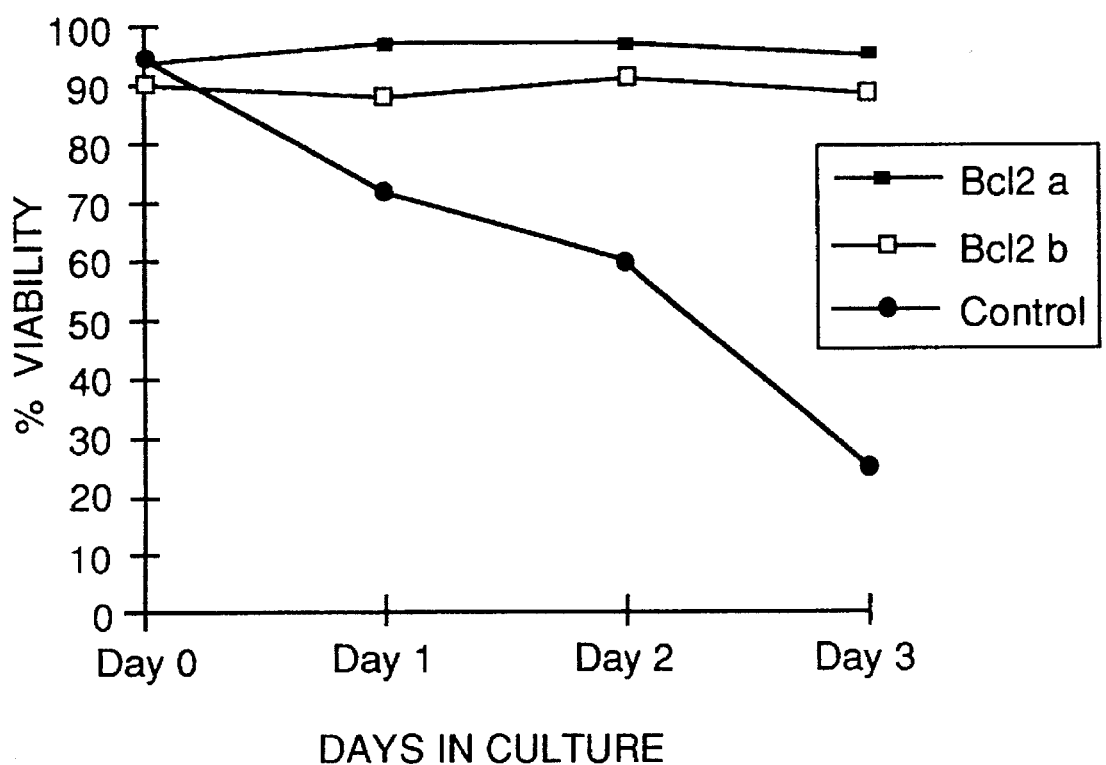
FIGS. 9a–c describes in vitro survival of neutrophils. Peritoneal cells from transgenic mice and control littermates were harvested after 4 hours of thioglycollate induced inflammation and cultivated for 24 hours to 3 days. 9(A) Viable neutrophils were counted on the indicated days using ethidium bromide/acridine orange treatment. 9(B) Two-color immunofluorescence contour plots of Mac-1 and Gr-1 expression on freshly isolated peritoneal cells (left panels) and after 3 days in culture (right panels). Neutrophils coexpressed Mac-1 and Gr-1 whereas monocytes or macrophages expressed only Mac-1. Percentages within each box of contour diagrams indicate the proportion of neutrophils. 9(C). DNA fragmentation of neutrophils in culture is described. Each lane represents DNA from 5×10$^6$ control or bcl-2 transgenic peritoneal cells isolated from a single mouse.
Figure 9B:
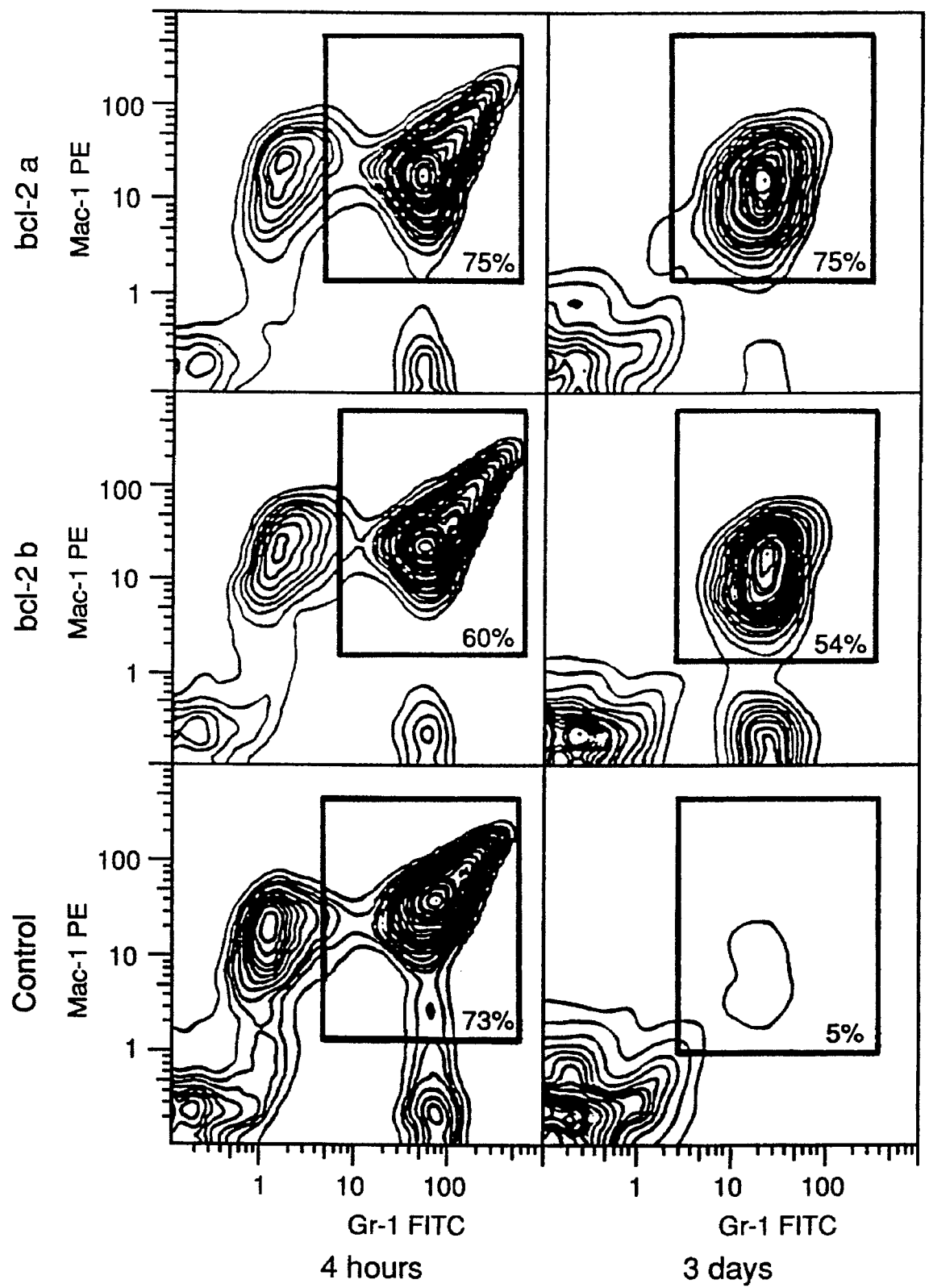
Figure 9C:
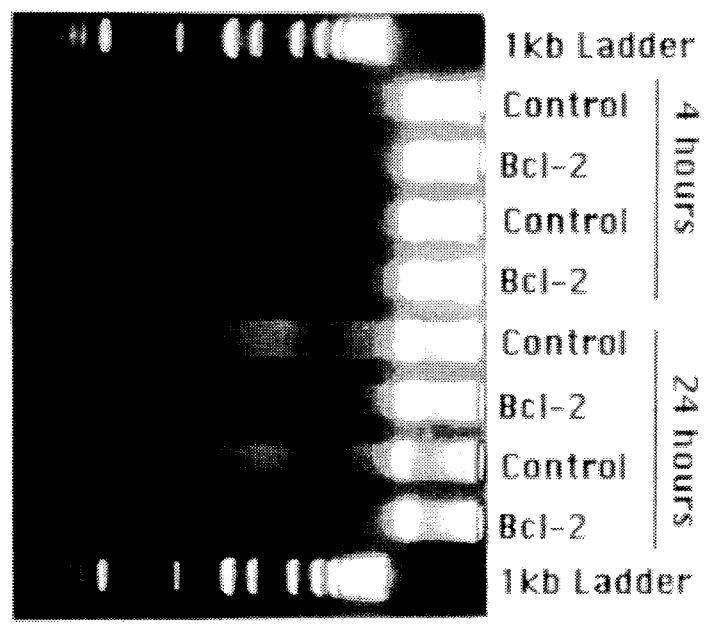

To assess the effects of bcl-2 expression on apoptosis, neutrophils were isolated from the peritoneal cavity during thioglycolate induced inflammation, and placed in culture. In culture, neutrophils normally undergo spontaneous programmed cell death characterized by morphological changes including nuclear pyknosis, chromatin condensation and cytoplasmic vacuolation (Wyllie, A. H. et al., 1980. Int. Rev. Cytol. 68:251). However, after 24 hours of culture, transgenic neutrophils expressing bcl-2 demonstrated markedly increased viability compared to control neutrophils (FIG. 9A). After 3 days in culture, bcl-2 expressing neutrophils remained viable whereas normal neutrophils did not survive. Fluorescence-activated flow cytometry analysis at day 3 confirmed the persistence of the bcl-2 neutrophil population in culture (FIG. 9B). Furthermore, transgenic neutrophils still stained for bcl-2 protein after several days in culture and did not display any of the morphological changes of apoptosis. Neutrophils undergoing apoptosis usually exhibit chromatin fragmentation in a characteristic internucleosomal pattern representing endogenous endonuclease activation (Savill, J. S., et al. J. Clin. Invest. 83:865). As shown by agarose gel electrophoresis of DNA extracted (FIG. 9C), fragmentation was inhibited in neutrophils expressing bcl-2, consistent with their enhanced survival capacity. In summary, expression of human bcl-2 under the control of the MRP8 promoter/enhancer region blocked programmed cell death of death of neutrophils in vitro.

Since the survival of the transgenic neutrophils was enhanced dramatically, it seemed likely that neutrophils homeostasis would also be affected. However, flow cytometry analysis revealed that the proportion of neutrophils in the blood flow did not differ significantly between transgenic and control mice (Table 1).

TABLE I

| Mice | Bone Marrow | Blood | Spleen |
| --- | --- | --- | --- |
| Nontransgenic | 30.4 ± 4.0 | 5.8 ± 2.8 | 1.8 ± 0.4 |
| Transgenic | 30.3 ± 8.3 | 12.6 ± 3.8 | 2.2 ± 0.4 |

Table I describes the neutrophil content in blood, bone marrow and spleen of control and transgenic mice. Neutrophils were counted by flow cytometric analysis of cells bearing Mac-1 and Gr-1 using two-color immunofluorescence. The results are expressed as arithmetic means (3 mice)±standard deviation (SD).

Figure 10:
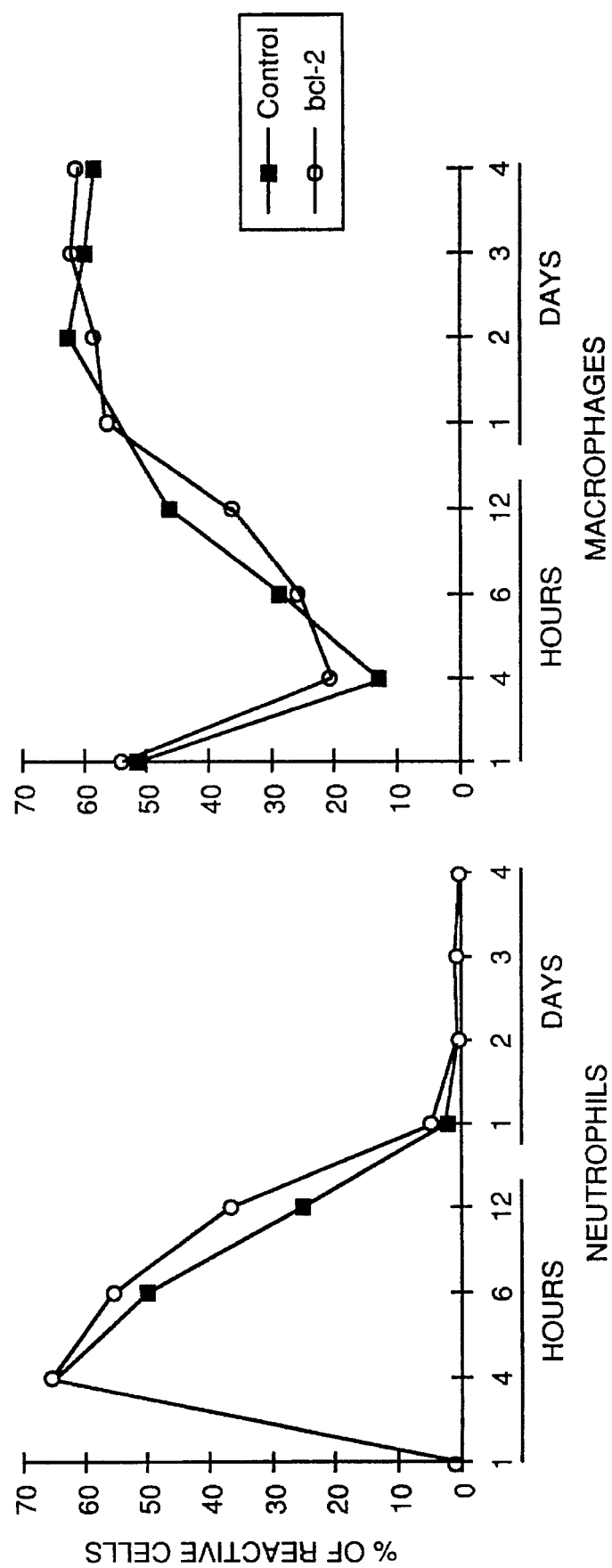
FIG. 10 describes neutrophil and macrophage populations during thioglycollate-induced peritoneal inflammation. Inflammation was elicited in the peritoneal cavities of control or bcl-2 transgenic mice using 3% thioglycollate broth. Exudate cells were harvested on the days indicated. The proportion of neutrophils and macrophages was calculated by flow cytometric analysis of cells bearing Mac-1 and Gr-1 (neutrophils) or only Mac-1 (macrophages) using two-color immunofluorescence.

The same was true for the total number of neutrophils (not shown) and the proportion of myeloid cells in bone marrow and spleen (Table 1). Therefore, constitutive expression of bcl-2 during the myeloid cell maturation did not result in the accumulation of neutrophils. Since the steady state number of neutrophils appeared unaltered in spite of their increased viability in vitro, we decided to examine their date in vivo. An acute inflammation was induced by injecting thioglycolate broth into the peritoneal cavity of 6 week old transgenic mice and control littermates (Lagasse, 1992 and Sanui, H., et al., 1982. Br. J. Exp. Pathol. 63:278). Cells were isolated from the peritoneal cavity at different times and analyzed by flow cytometry (FIG. 10). Several hours after the induction of inflammation, neutrophils accumulated at the inflamed site and became the predominant cell type. After 12–24 hours, the number of neutrophils gradually decreased and were rejected by macrophages in both transgenic and control mice. The resorption of neutrophils in the transgenic animal was consistently slower than for control mice and the difference was more marked in older animals (not shown). After 2 days, there were no neutrophils left at the site of the inflammation.

Figure 11:
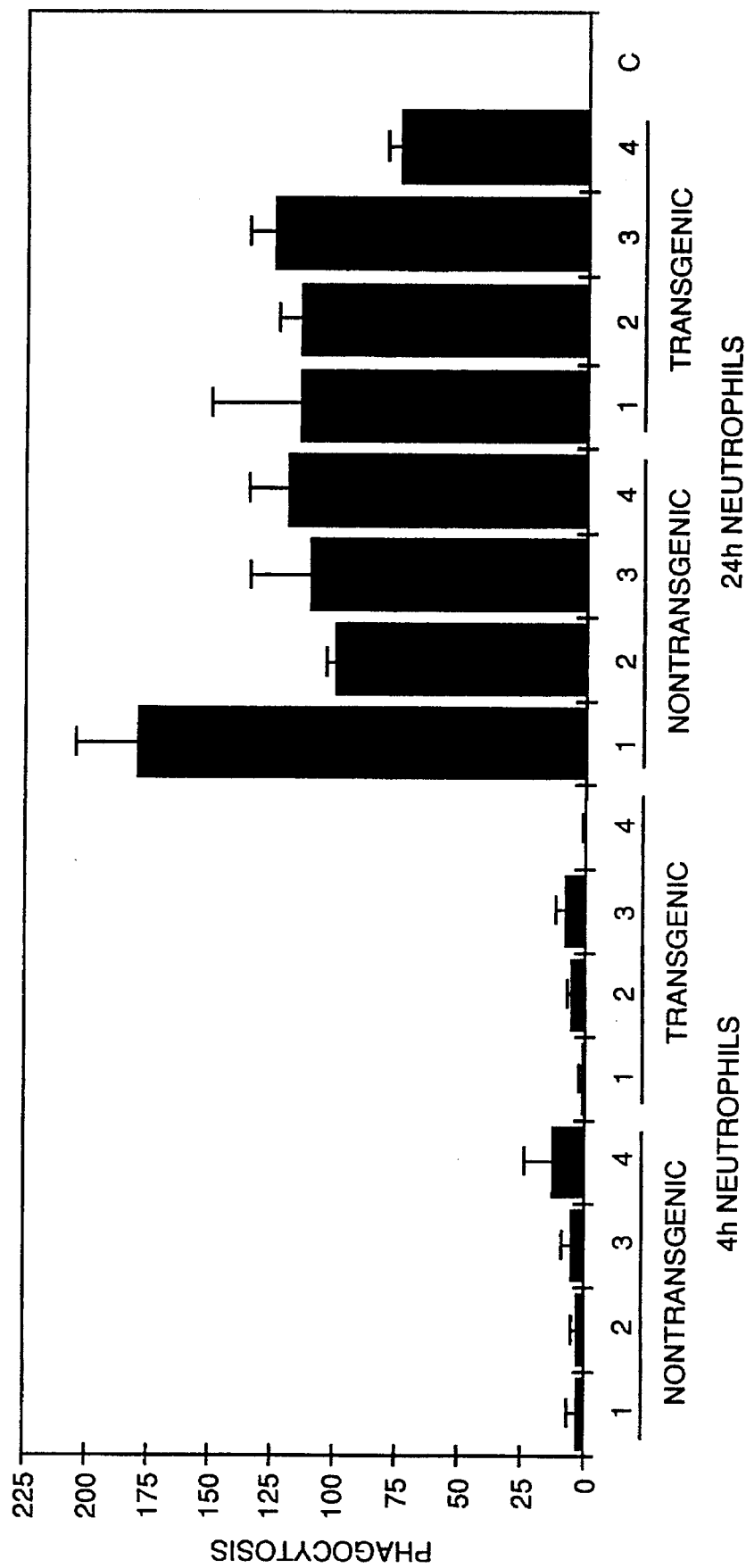
FIG. 11 describes phagocytosis of neutrophils by macrophages. Phagocytosis was evaluated by counting the number of macrophages ingesting neutrophils using inverted light microscopy. Each count correspond to the mean ±SD of 5 different randomly selected microscope fields per well. In the control (lane C) no neutrophils were added.

To investigate the relationship between neutrophil apoptosis and phagocytosis, we used an in vitro neutrophil-macrophage interaction assay (Newman, S. L., 1982. J. Exp. Med. 156:430; Fadok, V. A., 1992. J. Immunol. 149:4029). It has been previously reported that neutrophils aged for 24 h in culture spontaneously undergo apoptosis, and are concurrently recognized and engulfed by macrophages (Sayill, J. S. et al. 1989. J. Clin. Invest. 83:865). Neutrophils from control and transgenic mice were cultivated for 24 h and offered to thioglycolate-elicited macrophages. Phagocytosis of aged control and aged bcl-2 expressing neutrophils was identical (FIG. 11). However freshly isolated neutrophils were not phagocytosed by the macrophages. Thus, although thioglycolate-induced macrophages could not distinguish apoptotic from non-apoptotic neutrophils, they could distinguish aging neutrophils from freshly isolated neutrophils. This result suggests that, independently of apoptosis, neutrophils exhibit cell surface changes that allow them to be recognized and engulfed by macrophages. Example IV. Treatment of CFTR (–/–) by bone marrow transplantation from healthy CFTR+mice as a model for treatment of human cystic fibrosis.

The best available animal model for human CF is the CFTR Homozygous Knockout (–/–) mouse (Snouwaert, et al, (1992) op. cit.; and Dorin et al., (1992) op. cit.). These animals are characterized by failure to thrive, abnormalities of mucous and serous glands, and early death at between 30 and 50 days after birth. For these studies, the CFTR (–/–) mouse developed by Snouweart et al. and available from the Jackson Memorial Laboratory is used. The CFTR (–/–) mice are made immunologically incompetent by treatment with high doses of X irradiation or by the use of very young mice that have not yet acquired full competence. Bone marrow from CFTR (+/+) normal mice hematopoietic stem cells is introduced into the CFTR (–/–) mice by methods well known to those skilled in the art. The transplanted CFTR (+/+) hematopoietic stem cells are allowed to colonize the bone marrow of the CFTR (–/–) mice and produce progeny cells of the hematolymphoid system. The presence of the wild type CFTR protein in neutrophils in transplanted CFTR (–/–) mice is monitored by Southern analysis, ribonuclease protection assay, or monitoring electropysiological changes by detection of chloride ion transport relative to wild type cells. Reversal of the CFTR (–/–) phenotype by transplantation of wild type hematopoietic stem cells is monitored for increased survival beyond 30 to 50 days after birth, increased ability to thrive, reversal of alterations in mucous and serous glands and reduced obstruction of glandlike structures with inspissated eosinophilic material.

Example V. Gene therapy of cystic fibrosis phenotype with transgenic stem cells carrying the wild type CFTR gene under the control of the MRP8 promoter/enhancer.

The best available animal model for human CF is the CFTR Homozygous Knockout (–/–) mouse (Snouwaert, et al, 1992; Dorin et al, 1992) For these studies, the CFTR (–/–) mouse developed by Snouweart et al. and available from the Jackson Memorial Laboratory is used. The CFTR (–/–) mice are made immunologically incompetent by treatment with high doses of X irradiation or by the use of very young mice that have not yet acquired full competence. Bone marrow from MRP8-CFTR mice hematopoietic stem cells is introduced into the CFTR (–/–) mice by methods well known to those skilled in the art. The transplanted MRP8-CFTR hematopoietic stem cells are allowed to colonize the bone marrow of the CFTR (–/–) mice and produce progeny cells of the hematolymphoid system. The presence of the wild type CFTR protein in neutrophils of transplanted CFTR (–/–) mice is monitored by Southern analysis, ribonuclease protection assay, or monitoring of electrophysiological changes by detection of chloride ion transport relative to wild type cells. Reversal of the CFTR (–/–) phenotype by transplantation of wild type hematopoietic stem cells is monitored for increased survival beyond 30 to 50 days after birth, increased ability to thrive, reversal of alterations in mucous and serous glands and reduced obstruction of glandlike structures with inspissated eosinophilic material Example VI. Gene Therapy of Cystic Fibrosis phenotype by bone marrow transplantation from MRP8/bcl-2 host or by transplantation of transgenic MRP8/bcl-2 hematopoietic stem cells transfected in vitro.

To demonstrate the ability of bcl-2 expressing transgenic neutrophils to reverse the phenotype of CFTR mutation, the transgenic hematopoietic stem cells of the MRP8/bcl-2 transgenic mice are isolated and transplanted into the CFTR (–/–) mouse as the best available animal model for human CF. The best available animal model for human CF is the CFTR Knockout mouse (Snouwaert, et al, 1992; Dorin et al, 1992) For these studies, the CFTR (–/–) mouse developed by Snouweart et al and available from the Jackson Memorial Laboratory is used. The CFTR (–/–) mice are made immunologically incompetent by treatment with high doses of X irradiation or by the use of very young mice that have not yet acquired full competence. Bone marrow from MRP8/bcl-2 normal mice hematopoietic stem cells is introduced into the CFTR (–/–) mice by methods well known to those skilled in the art. The transplanted MRP8/bcl-2 hematopoietic stem cells are allowed to colonize the bone marrow of the CFTR (–/–) mice and produce progeny cells of the hematolymphoid system. The presence of the wild type CFTR protein in neutrophils in transplanted CFTR (–/–) mice is monitored by the methods described above for CFTR. Reversal of the CFTR (–/–) phenotype by transplantation of wild type hematopoietic stem cells is monitored for increased survival beyond 30 to 50 days after birth, increased ability to thrive, reversal of alterations in mucous and serous glands and reduced obstruction of glandlike structures with inspissated eosinophilic material. The transgenic animal expressing human bcl-2 at endogenous levels in mature myelomonocytic cells under the transcriptional and translational regulation of the MRP8 promoter enhancer region is an important component of the subject invention and provides a unique animal model for use in the treatment of cystic fibrosis as well as the treatment of other diseases of the myelomonocytic cells related to altered neutrophil proliferation and cell death such as the myelomonocytic proliferative, dysplasia and leukemic syndromes. The present invention offers several advantages over existing models.

The transgenic animals express wild type bcl-2 in early and mature myelomonocytic cells when under the transcriptional and translational control of the MRP8 promoter/enhancer region. The expression at endogenous levels of bcl-2 beyond the early stage of neutrophil maturation inhibits apoptosis and early cell death of the neutrophils. This transgenic animal is extremely valuable as a source of transgenic hematopoietic stem cells for use in gene therapy of CFTR mutation or deficiency in mice as a model of cystic fibrosis treatment. The transgenic animal of the subject invention is also valuable as a model of neoplasias of cells of the myelomonocytic series where expression of bcl-2 exceeds the endogenous level resulting in neoplasia. No other animal models provide wild type bcl-2 under the control of a promoter/enhancer region for expression in later stages of granulocyte development for the treatment of diseases caused by the early cell death of cells of the myelomonocytic series.

In addition, the transgenic HMRP8/bcl-2 neutrophils can be used to screen drugs or other treatments in vitro as inflamatory mediators and other pharmacologic actions and therefore will be valuable for drug discovery.

Example VII. Control of cell death in gene therapy of cystic cibrosis phenotype by bone marrow transplantation from MRP8/bcl-2/HVtk host or from transgenic MRP8/bcl-2/HVtk hematopoietic stem cells transfected in vitro.

Gene therapy of a cell degenerative disease such as cystic fibrosis in mammals such as a mouse or, preferably, a human involves expression of a cell proliferative and lifespan increasing open reading frame of interest, such as bcl-2, in the same cell, preferably neutrophils, as the expression of HVtk by transfecting hematopoietic stem cells of the host with at least one expression cassette such that both the open reading frame of interest and the HVtk gene are expressed from the same type of cell type specific promoter, such as MRP8. Treatment continues with the administration of a calibrated amount of gancyclovir, a substrate of HVtk. Enzymic conversion of gancyclovir to gancyclo-GTP kills dividing transgenic neutrophil precursors in the bone marrow and reduces the number of neutrophils recruited to the lung thereby reducing release of nucleic acids from dying neutrophils which causes the viscous mucous in CF patients.

Example VIII. Control of cell death in gene therapy of cystic fibrosis phenotype using MRP8/bcl-2 transgenic neutrophils expressing fas-FKBP fusion protein in the presence of FK1012.

The product of the oncogene, fas, induces apoptosis by a pathway independent of the bcl-2 regulated pathway. Apototic inhibition by fas is enhanced when the Fas protein forms a homodimer consistant with general biological control mechanisms of dimerization contributing to the activation of cell membrane receptors and transcription factors (Ullrich, A. and Schlessinger, J., Cell 61:203 (1990); Schlessinger, J., TIBS 13:443 (1988)). There is a need for a controllable method of fas activation and induction of apoptosis to induce the death of specific cell types such as the HMRP8/bcl-2 cells if overexpression of bcl-2 in these cells leads to neoplasia. An embodiment of the subject invention in which the life span of a cell, preferably neutrolphils, is controlled by homodimerization of Fas using the FKBP dimerization technique of Spencer, et al. ((1993) Science 262:1019–1024) in which a gene of interest such as fas is fused to the FK binding protein (FKBP) gene and the fusion protein product is dimerized by the binding of the FKBP portion to FK1012, a dimer and member of the family of compounds related to cyclosporin. Each FK1012 monomer moiety binds with high affinity to the FKBP thereby bringing together the protein fused to FKBP to form a protein dimer. Thus, Fas-activated apoptosis induction is achieved in the instant embodiment by the administration of FK1012 to kill all dividing and nondividing cells carrying the fas-FKBP fusion protein under the control of the MRP8 or MRP14 promoter/enhancer region or any promoter expressing in the cell type of interest. FK1012 is chosen for this purpose because of its ideal characteristics for a molecular "match maker" including lipid solubility, a lack of untoward cellular actions leading to toxicity, high affinity binding to its target receptor, and metabolic stability to allow for oral administration (Spencer, (1993), op. cit.). This allows apoptosis to be induced by the administration of FK1012 to the cell culture medium. The life span of neutrophils is shortened when necessary and in a controlled manner by the expression of the fas-FKBP gene fusion under the cell type specific expression control of a cell-specific promoter, preferably MRP8 or MRP14.

Example IX. Control of cell death in gene therapy using a safety system of cell killing genes and inducers.

A problem of gene therapy is the inability to remove the transplanted cells after transplantation into the host. In the event that the transgenic cells become pathogenic, no mechanism currently exists to rid the host of these pathogenic cells.

Further control of transgenic cell lifespan occurs by cotransfection of the herpesvirus thymidine kinase (HVtk) on a separate expression cassette utilizing the same cell type specific promoter as the transgenic open reading frame of interest or, optionally, on the same expression cassette and under the transcriptional and translational control a cell type specific promoter, such as MRP8 or MRP14, as the transgenic open reading frame of interest. In this embodiment, hematopoietic cells of a mammal, such as a mouse or, preferably, a human, are transfected with an open reading frame of interest that modulates the lifespan of the cell type of interest as a means of treating disease, preferably increasing the cell's lifespan, such as HMRP8/bcl-2. Included on the expression cassette is at least one, preferably both, of the cell death inducing genes, HMRP8/fas-FKBP fusion gene and HMRP8/HVtk gene capable of expressing in the same cell type as the open reading frame of interest, preferably neutrophils. The cell death inducing genes act as safety genes in this embodiment in the event that some or all of the transgenic cells become pathological due to the expression of the open reading frame of interest. Administration of the drugs, gancyclovir and/or FK1012 results in the death of the transgenic cells. Gancyclovir primarily kills dividing cells thereby ridding the transgenic animal of cells that are proliferating to the detriment of the host. For example, the ablation of neutrophils in the bone marrow of the host, preferably a human, by gancyclovir administration is performed to reduce neutrophil recruitment in cystic fibrosis. In another example of the invention, treatment the the mammalian host, such as a mouse or, preferably a human, with FK1012 results in fas-FKBP fusion protein dimerization and induction of apoptosis in nondividing and dividing cells providing a means of reducing or eliminating proliferation of the transgenic cells. In another embodiment of the invention, treatment of the mammalian host, such as a mouse, or preferably a human, with both gancyclovir and FK1012 results in the cell death of all transgenic cells of the gene therapy, including those transgenic cells in the bone marrow where the immature cells of the hematolymphoid system are dividing and those transgenic cells that are circulating and no longer actively dividing. This example allows the killing of all cells expressing the safety genes comprising HVtk and fas-FKBP such that the host, preferably a mouse or, most preferably a human, is rid of the transgenic cells in the event that the transgenic cells become pathological and present a danger to the host. The use of controlled cell death in gene therapy as a means of removing the transgenic cells from the host following gene therapy is unique in the art and fills a long felt need for such a safety mechanism.

Example X. Reconstitution of normal neutrophil function using gene therapy.

Transgenic hematopoietic stem cells expressing the healthy gene deficient in the patient under the control of MRP8 or MRP14 are prepared and transplanted into affected animals for reconstitution of normal neutrophil function. Chronic Granulomatous Disorder (CGD), an immunodeficiency due to defective NADPH oxidase results from mutations in the genes encoding the protein gp91-phox, p22-phox or p47-phox or p67-phox which are expressed in neutrophils (Porter, C. et al. (1993) Blood 82:2196–2202; Cobbs, C. et al. (1992) Blood 79:829–1835; Erikson, R. et al. (1992) J. Clin. Invest. 89:1587–1595; DiBartolomeo, P. et al. Bone Marrow Transplantation (1989) 4:695–750). The reversal of symptoms of Chronic Granulomatous Disease phenotype following reconstitution by gene therapy is monitored as regained NADPH oxidase activity.

Neutrophil Specific Granule Deficiency (NSGD), a congenital disorder associated with impaired inflammatory response and a deficiency of several granule proteins such as lactoferrin, vitamin-B-12 binding protein, defensin, and gelatinase (Lomax, K. J. et al (1989) J. Clin. Invest. 83:514–519) is reversed by transplantation of transgenic hematopoietic stem cells carrying the gene of a granule protein under the control of the MRP8 or MRP14 promoter/enhancer. The gene encoding alpha-1-antitrypsin is cloned into an expression cassette under the control of MRP8, used to produce transgenic hematopoietic stem cells and transplanted into animals deficient in alpha-1-antitrypsin for treatment of hereditary emphysema. The gene encoding myeloperoxidase is cloned into an expression cassette under the control of MRP8, used to produce transgenic hematopoietic stem cells and transplanted into animals deficient in myeloperoxidase for treatment of Hereditary and Acquired Myeloperoxidase Deficiency.

Example XI. A mouse model of human myelomonocytic leukemia.

A transgenic animal, such as a mouse, is generated by cloning an oncogene, such as c-myc, rxr, pml/rarα, into an expression cassette under the control of MRP8 promoter/enhancer and introduced into hematopoietic stem cells. The hematopoietic stem cells are introduced into normal immunoincompetent animals for the production of transgenic animals having the phenotype characteristic of human myelomonocytic leukemia myeloproliferative disorder. The animal model is used to test drugs and other new therapeutic approaches for treatment of the disease by administering the test drug to the transgenic myelomonocytic leukemia mouse and monitoring for changes in the phenotype toward a normal state.

Example XII. Treatment of thymic T cell loss due to HIV infection.

Human immunodeficiency virus (HIV) disease is typified by declining CD$^+$T lymphocyte counts in the peripheral circulation, a loss which may be secondary to accelerated destruction, to suppressed differentiation, and/or to sequestration of circulating cells into tissue spaces. The immunodeficient SCID-hu mouse (McCune et al, 1988, 1991) containing human hematolymphoid organs that promote long-term multilineage human hematopoiesis and are permissive for infection with HIV. Human thymopoiesis is suppressed by HIV infection, thereby precluding regeneration of the peripheral T-cell compartment. Human thymopoiesis suppression by HIV is treated by the transplantation of transgenic human hematopoietic stem cells expressing bcl-2 from a lymphoid cell-specific promoter into the HIV infected SCID-hu mouse. Increased circulating CD$^+$T lymphocytes are monitored by methods known to those skilled in the art as a measure of reversal of human thymopoiesis suppression by HIV. The combined use of the previously existing animal model of human immunodeficiency (SCID-hu) and an embodiment of the subject invention provide a powerful tool to test a possible treatment for a human disease, AIDS. Further, infection of monocytes by HIV resulting in monocyte loss is suppressed by introduction of MRP8/bcl-2 into monocytes since MRP8 expresses in this cell type.

All publications and patent applications mentioned in this specification are herein incorporated by reference to the same extent as if each individual publication or patent application was specifically and individually indicated to be incorporated by reference.

The invention now being fully described, it will be apparent to one of ordinary skill in the art that many changes and modifications can be made thereto without departing from the spirit or scope of the appended claims.

SEQUENCE LISTING

What is claimed is:

1. A method for increasing the lifespan of a mammalian hematolymphoid cell in vitro, said method comprising:
   introducing into a hematopoietic stem cell a nucleic acid construct to produce a transgenic hematopoietic stem cell wherein
   said nucleic acid construct comprises:
   i) a hematolymphoid cell specific transcriptional initiation region, and
   ii) an open reading frame from a gene which when expressed increases the lifespan of a hematolymphoid cell,
   and growing said transgenic hematopoietic stem cell to produce a hematopoietic stem cell, and wherein
   the lifespan of said hematolymphoid cell is increased at least approximately 1.5 fold relative to a control cell.

2. The method of claim 1, wherein said hematolymphoid cell specific transcriptional initiation region is selected from the group consisting of MRP8 and MRP14.

3. The method of claim 2, wherein said open reading frame is a coding sequence from a mammalian bcl-2 gene.

4. The method of claim 3, wherein the lifespan of said hematolymphoid cell is increased at least approximately 2 fold relative to a control cell.

5. The method of claim 1, wherein said hematolymphoid cell is a myeloid cell.

6. The method of claim 5, wherein said myeloid cell is a granulocyte.

7. The method of claim 6, wherein said granulocyte is a neutrophil.

8. The method of claim 1, wherein said hematopoietic stem cell is a human cell.

9. A transgenic mammalian myeloid cell comprising a nucleic acid construct, said construct comprising:
   i) a transcriptional initiation region from a gene selected from the group consisting of MRP8 and MRP14, and
   ii) an open reading frame from a gene which when expressed increases the lifespan of said myeloid cell by at least approximately 1.5 fold.

10. The transgenic mammalian myeloid cell according to claim 9, wherein said open reading frame is a coding sequence from a mammalian bcl-2 gene.

* * * * *

SEQUENCE LISTING ( 1 ) GENERAL INFORMATION:

( i i i ) NUMBER OF SEQUENCES: 6

( 2 ) INFORMATION FOR SEQ ID NO:1:

( i ) SEQUENCE CHARACTERISTICS:
        ( A ) LENGTH: 4195 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:1:

```
TTCCACCTTT  TGGCTCTTGT  AAATAATGCT  GCTATGAACA  TGAATGTACA  AACATCTGTT      60
TGAATCCCTG  CATTCAATTC  TTTTGCATAT  ATACCCAGGA  GCAGAATGAT  GGATCATATG     120
GTAATTCTGT  GTTTATTTAT  TTGAGGAACA  AACTTGCCGT  TTTCCATAAC  AGCTGCACTA     180
TTTTACATTC  CCACTAACAG  TGCATTAGGC  TTCCAATTCT  CTATGCCCTC  ACCAACACTT     240
GTTTTCTGGG  TTTTAAAAGA  AGTAGTAGTC  ATCCTTGTAG  GTGTCAGGTG  GTATCTCATT     300
GTCGTTTTGC  TTCATGTTTT  CCTAAAGATT  AGTAATTTTC  ATATGCTTAT  TGACCATTTG     360
TATATCTTCT  TCGGAGAAGT  GTCTATTTGA  GTCTTTCCCC  AATTTTGATT  GGTTTGTTTG     420
TTTTTTGTTG  TTGAGTTGTA  GGGATTCTTT  TATATTCTGG  ATATTAATCC  CTTATCAGAT     480
ATTTGTTTTA  CAAATATTTT  CTTTGTAACA  ACAGAAACAC  ACCACAGTCT  TCAAGGTTGG     540
AAGCCAGTTA  ATCTGAGTAG  CATTTGTTA   GTGGTGGGGA  GAGGATTTGT  TCCTCCTGAA     600
ATCCTGGGGA  ATTGGCCACC  TCCTCTTCTC  CTCTTAGGCA  TGAAGCGCGT  CTGGCTTCTC     660
CAAAGAACTC  TTCCCCTCCA  CTACCTCAGA  GTTAGCTTCC  TCTCTTCAGC  CAGTGATCCT     720
GGGGTCCCAG  ACACAATAAT  TAACCAAGAG  AGGGTGAAAG  GCTCCTGCT   GTGTTTATGC     780
AATGGCTCAG  GCCCTTGTGA  AGTGCCGAGG  GACCCAAGC   AGCCTCCATC  TCCCAGGGCA     840
TGGTCCATCC  CCAGCTTTCA  CAGAACAGGA  AAGCTGTGGA  GGAGTGTGGG  CAGCAGGGTA     900
GGAATGGATA  TAGCCCTTGG  CAACAACACA  TTTCCCCACA  AAGCACCCAC  CCAAAAGAAC     960
AACAACGATA  GTTTAGTTT   TTAGTAATGA  GAACAATAGT  TCTCATGACT  AAAAGCCATC    1020
```

```
AGCCAGGACA CTGTTCTCAA CCCTTTTGCG GTCTTTGGAC CCTTTGAAAC TCTGACAGAA    1080
GCCATGGAGG AATGTTCTCA CTGAGTGCAT GCACTCAAAA TGATGCATTC AACTTCAATT    1140
CAGTTTCAGG GATGTATGGC CTGACCACCA ATGCAGGGGA TTAGCAATCG CAATAGTGGA    1200
GAGGGCATGG GAGTGGGAAT CTGGCTGGAT CAAGCAAGTG GATGCCAGCA GCCCAGAAAA    1260
AGAGCCCCCC TACCTGCTTT TTCCTTCCTG GGCACTATTG CCCAGCAAAT GCCTTCCTCT    1320
TTCCGCTTCT CCTACCTCCC CACCCAAAAT TTTCATTCTG CACAGTGATT GCCACATTCA    1380
CTGGTTGAGA AACAGAGACT GTAGCAACTC TGGCAGGGAG AAGCTGTCTC TGATGGCCTG    1440
AAGCTGTGGG CAGCTGGCCA AGCCTAACCG CTATAAAAAG GAGCTGCCTC TCAGCCCTGC    1500
ATGTCTCTTG TCAGCTGTCT TTCAGAAGAC CTGGTAAGTG GGACTGTCTG GGTTGGCCCC    1560
GCACTTTGGG CTTCTCTTGG GGAGGGTCAG GGAAGTGGAG CAGCCTTCCT GAGAGAGGAG    1620
AGAGAAAGCT CAGGGAGGTC TGGAGCAAAG ATACTCCTGG AGGTGGGGAG TGAGGCAGGG    1680
ATAAGGAAGG AGAGTATCCT CCAGCACCTT CCAGTGGGTA AGGGCACATT GTCTCCTAGG    1740
CTGGACTTTT CTTGAGCAGA GGGTGGGGTG GTAAGGAAAG TCTACGGGCC CCCGTGTGTG    1800
TGCACATGTC TCTGTGTGAA TGGACCCTTC CCCTTCCCAC ACGTGTATCC CTATCATCCC    1860
ACCCTTCCCA CCAGAGGCCA TAGCCATCTG CTGGTTTGGT TATTTGAGAG TGCAGGCCAG    1920
GACAAGGCCA TCGCTTGGGG CATGAATCCT CTGCGTACTG CCCTGGCCAG ATGCAAATTC    1980
CCTGCCATGG GATTCCCCAG AAGGTTCTGT TTTTCAGGTG GGGCAAGTTC CGTGGGCATC    2040
ATGTTGACCG AGCTGGAGAA AGCCTTGAAC TCTATCATCG ACGTCTACCA CAAGTACTCC    2100
CTGATAAAGG GGAATTTCCA TGCCGTCTAC AGGGATGACC TGAAGAAATT GCTAGAGACC    2160
GAGTGTCCTC AGTATATCAG GGTGAGGAGG GGCTGGGTGT GGCGGGGGCT CTCTGCCTGG    2220
TCCTGGGGCT GCCCTGGGCC AGCGGTCCTC CCTGCCACCC TTCATAGATG CTATGCCTCG    2280
GCTCTCTCTG AGATCTTTAA ACTCTGGCTT CTTCCTCCTC AATCTTGACA GAAAAGGGT    2340
GCAGACGTCT GGTTCAAAGA GTTGGATATC AACACTGATG GTGCAGTTAA CTTCCAGGAG    2400
TTCCTCATTC TGGTGATAAA GATGGGCGTG GCAGCCCACA AAAAAGCCA TGAAGAAAGC    2460
CACAAAGAGT AGCTGAGTTA CTGGGCCCAG AGGCTGGGCC CCTGGACATG TACCTGCAGA    2520
ATAATAAAGT CATCAATACC TCATGCCTCT CTCTTATGCT TTTGTGGAAT GAGGTTCCTC    2580
GGTGTGGAGG GAGGGTTGGA AAACCCAAAG GAAGAAAAAG AAATCTATGT TATCCCACCC    2640
TACCTCTCAC AAGCCTTTCC TGCTTTACCC CTCACCTGGC CTCTGCCCCA CATTCCTTCA    2700
GCCCCTCATT TCGAGCATTG GATTTGAGGC TTAAGGATTC AAAAAGTCGT CATGAATATA    2760
GCTGATGATT TTATAGTGGT TCTGAAATGG GTCGGGGATT TGGGAACAGG GTGGTAGTAT    2820
AAGAACAACT GATACTGTTC TCTAAGCTAA ATCTTAGCTT CCAGCTACCT GTCTTAGATG    2880
TGGCTCTTGG GAACCTTAGA GTGATAGCTA CATAGAAGTG TGTGGGTGTG TGTGTGTGTG    2940
TCTGTGTGTG TGTGTGTGAG AGAGAGACAG ACAGAAAGAG AGCAAGAGAG GGAAGGGGGG    3000
AGAGGCTGAT TGTGTGTGTG GTGTGATGTA GGTGGACAAT GTTCAGAGTC CTCCATTAAC    3060
AGGATAATCC TCACACCTGT CCACATACCT GTAGTTTGTC CTTGGGGATT TTGAAATTT    3120
TTCCTCCCTC TCCACTCCCA AACTCCCAAC TCAATTAAAT GATAAAGGAA TAGGCAAATA    3180
GGAAAATAAA TTAGTAAAAC TTAAGTCAAA GAATAGGTTA TTCATACGCT GCCTATGGGA    3240
TTCTATGCTT TGTGATCAGA AAATTATCTA AAAAATACTT CCCAAGGGCT GGTACAAGGG    3300
AGGCCAGAAG ACGAGTGGTT CTTCTCTGAG GTGGACATTA AAAAAGAAG AAAATGAAGG    3360
GGAACCTTTT GACAAGAATG TCACCCCAAA CTGGATTTTC ATGCTGTGGT GTGGGGAATT    3420
```

-continued

```
TTCTGTTGTC CTCACTTAGG TGCTGGGGCA GTGGTGTTAG TGATGGGTAA AAAGGTAGGA      3480

AGCTGTCACA GAATCACTAA ACCAGGGTTC TTAACTTGTC TGTCTATACA TCTCTGAAAT      3540

TGGGTTGAAG TTGTGTGCAT CATTTTGAGT GACGCACTGA GAACATTCCT CCACGGCTTC      3600

CATCGAGAGT CTCGAAAAGG CCCAACACCT CAAAAAGGTT AAGAACACTT GTCCTGCTTA      3660

CTGGTTTTTA GTAACAAATG GCAGAGTATT TCTCTCTGTC TCTCTCTCTT TTTTTTTTT      3720

TTTTTTTGAG ACACAGGGTC TTGTCTGTCA CGTGGACTAG AGTACAATGG GCATGATCAT      3780

GGGCTCACTG TAGCCTCGAA CACCTGGGCT CAAGTAATCC TCCCACCTCA GCCTCTTTAG      3840

TAGCTGGGAC TACAGCATGA GCCACTGCCC TTGGCTAATT TTTAAATTAT TTTTTTGTAG      3900

AGATGGAAAC TTGCTATGTT GCCCAGGCTA GTCTCAAACT CCTGGACTCA AGCGATCCTC      3960

CTACCTTGGC CTCCCAAAGT GCTGAGATTA CAGTGTGATC CACACCACAC CTGGCCAAAG      4020

ATTGGAGTAT TTTTATTGCT ATTGTTGTGC TGGGTGGGTG GGTGGGTGTA TGCTTTGTGG      4080

GGACGTGTGT TGTTGCCAAG GGCTAAATCA GTTCCTACCC TGCTGCCCAC AGTCCTCCAC      4140

AGCTTTCCTG CTCTGTGAAG CTAAGGATAC ACCCCGATGA TAAGCTGTCA ACATA           4195
```

( 2 ) INFORMATION FOR SEQ ID NO:2:

( i ) SEQUENCE CHARACTERISTICS:
        ( A ) LENGTH: 47 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Met Leu Thr Glu Leu Glu Lys Ala Leu Asn Ser Ile Ile Asp Val Tyr
 1           5                  10                  15

His Lys Tyr Ser Leu Ile Lys Gly Asn Phe His Ala Val Tyr Arg Asp
            20                  25                  30

Asp Leu Lys Lys Leu Leu Glu Thr Glu Cys Pro Gln Tyr Ile Arg
        35                  40                  45
```

( 2 ) INFORMATION FOR SEQ ID NO:3:

( i ) SEQUENCE CHARACTERISTICS:
        ( A ) LENGTH: 46 amino acids
        ( B ) TYPE: amino acid
        ( D ) TOPOLOGY: linear ( i i ) MOLECULE TYPE: protein ( x i ) SEQUENCE DESCRIPTION: SEQ ID NO:3:

```
Lys Lys Gly Ala Asp Val Trp Phe Lys Glu Leu Asp Ile Asn Thr Asp
 1           5                  10                  15

Gly Ala Val Asn Phe Gln Glu Phe Leu Ile Leu Val Ile Lys Met Gly
            20                  25                  30

Val Ala Ala His Lys Lys Ser His Glu Glu Ser His Lys Glu
        35                  40                  45
```

( 2 ) INFORMATION FOR SEQ ID NO:4:

( i ) SEQUENCE CHARACTERISTICS:
        ( A ) LENGTH: 4440 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:

-continued ( A ) NAME/KEY: misc_feature
( B ) LOCATION: 2738
( D ) OTHER INFORMATION: /note= "Nucleotide indicated as "N"
represents a region of 360 base pairs which do not
appear in Figure 2."

( x i ) SEQUENCE DESCRIPTION: SEQ ID NO:4:

| | | | | | | |
|---|---|---|---|---|---|---|
| ATCACTGTGG | AGTAGGGGAA | GGGCACTCCT | GGGGTGGCAA | GGTGGGAGGT | GGGCCCTGTG | 60 |
| TTCCCACAGT | GGGCAGGGAG | GTAGTGAAAG | GGAAGCTGGC | CGGACAGGAA | GGGCCATTCC | 120 |
| AAGAGGGCTT | TGTGCGCAGG | GCTAAGCCAA | GCTTTCTCCA | TAGGCAATGG | GGAGCAACTG | 180 |
| GAGGTTCGTA | GCAGGAGAAG | GACACATCAA | GCCCACCAGG | AGGCTAAGTA | AAAACAGTTG | 240 |
| TCTCCCAAGT | TATAAGTTCC | TGGAACCCTT | GCTGGGAGCA | GGATTTAGAA | AAATGATGCT | 300 |
| GAGAGATGCT | AGAAACATAT | TCGCCCTGAG | GCTCTCTCAC | TCAGACTGCA | AGAGGAAGGT | 360 |
| ATCATCAGAA | TTGCCCTTAA | CCAGGAACCA | GAATAGCTGG | GTCCCCTTCC | TGCCAAGTCA | 420 |
| GCAACCAGCT | ATGTGACCTT | GCTCAGGTCC | ATCTCCGGGT | GTCAGTTTCT | TCATCTACAA | 480 |
| TGCAAGAGGG | TTGCCCACCT | CTGAGAACCC | TTCTAACCCC | AAATCTCACC | CTATGAATCT | 540 |
| AAGAACACAA | CCCCTCGCCA | TCCTAAGTAT | CACAGAGCCA | GGCAAGCATG | GGTGAGAGCT | 600 |
| CAGACCATCC | TTGTTGGACT | AAAAGGAAGG | GGCAGACTGC | CATGGGGGGC | AGCCGAGAGG | 660 |
| GTCAGGCCCC | CATAGGTCCT | CAGCCTGCTT | CAACCTCAAA | GGGGATGGGG | GGCTGAGTGG | 720 |
| TGCCAGAGGA | GCAGCAGGCT | CGCTCGGGGA | GAGTAGGGCC | TTAGGATAGA | AGGGAAATGA | 780 |
| ACTAAACAAC | CAGCTTCCTG | CAAACCAGTT | TCAGGCCAGG | GCTGGGAATT | TCACAAAAAA | 840 |
| GCAGAAGGCG | CTCTGTGAAC | ATTTCCTGCC | CCGCCCAGC | CCCCTTCCTG | GCAGCATTAG | 900 |
| CACACTGCTC | ACCTGTGAAG | CAATCTTCCG | GAGACAGGGC | CAAAGGGCAA | GTGCCCCAGT | 960 |
| CAGGAGCTGC | CTATAAATGC | CGAGCCTGCA | CAGCTCTGGC | AAACACTCTG | TGTGGCTCCT | 1020 |
| CGGCTTTGGT | AAGTGAGCTG | CCAGCTTCCC | CAGGCAGAAG | CCTGCCTGCC | GATTCCTTCT | 1080 |
| TTCCTTCCCT | GACCCAACTT | CCTTCCAAAT | CCTCCTCCTA | GAAGCCCTCC | TTGGTTGGCC | 1140 |
| CTGCCTACTT | TAAAGCTTCT | TTCACATTTT | CTTAGGTCAT | GTTCCCCTGG | GGCCTCCTGC | 1200 |
| CCTCAAATGC | TTTGCTTTTT | GGCACTCTGT | AGATATTCTA | AAAAATCATT | TTGTACATGT | 1260 |
| GTGTGACAGG | CCATCTCCCA | GTTAAGTTGC | AGCCTGTGCT | TTCTTTTTAT | TTTGCACTTC | 1320 |
| CCCCACTATT | TCTGTGAGTG | CTTAGTAGGA | AGTGTCAAAG | AAGCTTGACA | GCATTTTCTT | 1380 |
| CTAAGTGTCC | CAACTCTTGG | TTTTCCATTA | CACAGACAGA | GTGCAAGACG | ATGACTTGCA | 1440 |
| AAATGTCGCA | GCTGGAACGC | AACATAGAGA | CCATCATCAA | CACCTTCCAC | CAATACTCTG | 1500 |
| TGAAGCTGGG | GCACCCAGAC | ACCCTGAACC | AGGGGGAATT | CAAAGAGCTG | GTGCGAAAAG | 1560 |
| ATCTGCAAAA | TTTTCTCAAG | GTAGGGCTGG | ACTCTGGCAG | GTCTGACCCA | GCCTCACCGC | 1620 |
| AGTTTGGGTT | GACAAGGGAG | GATGGGAGTA | TGGGCTACAG | CAATCAAGGG | GAAGATTTGA | 1680 |
| GCTCCTGGAG | CCCAGCCCCA | AGACGCAGCG | AGTGTCCTGT | TATACAGGGC | AGGTGCTCAC | 1740 |
| AGTTACACAG | GACGACAGGG | TCAAGAAATT | GCTCAATTGA | ACACCTGCTA | TTTGTCGGGC | 1800 |
| CCTGTTCTGG | GCAGAGGGAT | GTAGTGGTAA | ATGGGAGCCC | ACTATTCCAT | GAGGAGACAC | 1860 |
| ACAGTAAAGT | TGTTGGCCAA | TAAAGAGCAC | AGATAAAGCC | AAATGCCAAT | AAGTGCCTGG | 1920 |
| AAGAAAATGA | GATAGAGTGC | GCTGTGGGCA | ATGGGGCTGG | GTGGGGTGGA | GGTGACCAGT | 1980 |
| TAGGGTACAT | GAGAAGGGCC | TCTTTGAGGA | GGTAACATTT | GAGCTGAGCC | CCGAATGTTG | 2040 |
| GGGAGGGAAG | CCCCTGAGGA | TGACACTTGG | CACAAAGCTG | AGGAGACCCT | AAGCCTCAGG | 2100 |
| GCGAACTTGG | GGTGGAAGAC | TTGGGGGCTT | TTCTAATCCT | AAGGGTCTGC | GGTGGAAAAT | 2160 |

```
GAATGCATAA  AGAGCACATG  GAGAGCACCT  GCACAGCACT  CAGGGAACTG  GGAGGTTTTT   2220
CCCCCGCTCC  AAAAATGATT  AGGCAGTTCT  AAGAAAAAGG  CTGAGCACTT  CCAACAGCCT   2280
TTTTGTTTTC  TTTTCAAATT  TGGGGAAAGT  CGGGAAACAG  AGGCCTGCAT  TAAGAAGGGT   2340
GGAACACATG  GGTCTCAGTC  TCAGTTCCAG  TCCCGGAGCC  AGACATCCTG  GGGTAGGTCC   2400
CCAGCCCTCC  CAGTGCCCCT  CCCTCCGCCT  TGGTAAGGTG  GAGAATTGCA  GCCTTCAGAG   2460
TTAGGGGCCC  TGACAGCTCT  CCATAGGTGG  AGGCCTCAGG  CAGGCAGGAT  GCTGGGTGGG   2520
GTAGGCAAGA  AAGGGCCCAG  CAGAGAGGCC  GCATCGGAAA  ACTATCCTCC  ATGTGACCCC   2580
CTATGCCCGC  TTCACCCCCC  ACCTGACATC  CCCCACCAGA  AGCAAAGCGA  TGCTGTGGGA   2640
AAGGAAGCAG  AGCCTCATGG  ATGGGCTGCA  CAGGAGAGTG  CTCGCATTGG  CTGGGTACCC   2700
CACAGGTTCT  GGGAGGGGAC  TTAGCGAGGT  GACTCAGNTG  CCTCGGCCTC  CCAAAGTGCT   2760
GGGATTACAA  GCATGAGCCA  CCCTGTCCGA  CCATCTCCCC  TTTTATACTT  TATCACACCC   2820
TTGAGGTCAG  CGGAGCACAT  ACTCTGCTCT  CTGACCCTCC  ATCTCCCCTG  CCCACACCTA   2880
GGTTTTTCTA  GTGTTTCCCC  GTTGTATTGG  TTGAAATAAG  TTTCACTAAT  TGGTAACCTC   2940
CAGAGGGAAG  GGAAGGGAGG  GCAGGGGAAG  GAGTGAAGTG  CAGAGGGGTA  GCAGAGTGGA   3000
ACTGGCCTCT  AAGTCAGATC  TGAATTTGCA  TGCCCTCAAT  AGTCAAGCCT  GTGAAAACTA   3060
ATGACCCTCT  CTAGGACTGG  TTTCAAGTCT  TCCTCCAGGA  AGATACCATT  CCTAGCTGTT   3120
AAAGTTGTTA  TAAGGACCAA  ATGAGGTGAC  ATTTCCAGGC  TTACTCATGC  CATGACCAGG   3180
GCAAGACCCT  GGAACTCAGC  TTCCTCTTCT  ATAAATAGAG  AATCAGCACC  CAAGTCACAG   3240
GGTCATGGAG  GGAATAAACT  GGAGAGCGTT  TGGTATGTGC  TCAGTGTCTG  CTCCATTGTG   3300
CGCACTCAGC  CTATGGTCAT  TTTTAATTTT  TAAATCCAGC  CCCAGGGTCG  AGGCTTCCTT   3360
GTACATTTGC  CAGCTGGTCA  TTTACTGTGC  TCCCAGTCCC  CACCTCTGGC  CACACCCAGC   3420
TCTCACAGCC  TTCTCTCCCC  ACCCGCAGAA  GGAGAATAAG  AATGAAAAGG  TCATAGAACA   3480
CATCATGGAG  GACCTGGACA  CAAATGCAGA  CAAGCAGCTG  AGCTTCGAGG  AGTTCATCAT   3540
GCTGATGGCG  AGGCTAACCT  GGGCCTCCCA  CGAGAAGATG  CACGAGGGTG  ACGAGGGCCC   3600
TGGCCACCAC  CATAAGCCAG  GCCTCGGGGA  GGGCACCCCC  TAAGACCACA  GTGGCCAAGA   3660
TCACAGTGGC  CACGGCCACG  GCCACAGTCA  TGGTGGCCAC  GGCCACAGGC  CACTAATCAG   3720
GAGGCCAGGC  CACCCTGCCT  CTACCCAACC  AGGGCCCCGG  GGCTGTTATG  TCAAACTGTC   3780
TTGGCTGTGG  GGCTAGGGGC  TGGGCAAAT   AAGTCTCTTC  CTCCAAGTCA  GTGCTCTGTG   3840
TGCTTCTTCC  ACCTCTTCTC  CAACCCTGCC  TTCCCAGGGC  TCTGGCATTT  AGACAGCCCT   3900
GTCCTTATCT  GTGACTCAGC  CCCCTCATTC  AGTATTAACA  AAATGAGAAG  CAGCAAAACA   3960
TGGGTCTGTG  CTGGGCCCCT  TGGCTCACCT  CCCTGACCAT  GTCCTCACCT  CTGACTTCAG   4020
GCCCCACTGT  TCAGATCCCA  GGCTCCCTGC  CCATCTCAG   ACACCCTGTC  CAGCCTGTCC   4080
AGCCTGACAA  ATGGCCCTTG  TCACTGTACA  CTGTAGAAAG  CAAAAAGGCA  TATCTCTACC   4140
CCTTGATATG  CCTGCTACCT  CACCAACCAG  CCCCAAGCCT  GTCTTCACCC  ATCACTGTCT   4200
ACACAGCCCT  CTCTCTCTCC  TAACAGAATT  CTATTCCTCT  GAAAGTCTTC  AGAAACTGGA   4260
CCTAGATAGT  GCCATGTCTG  GGAGGAATA   TGGCACCAGG  CAGTGGAAAC  AAGGACAGAT   4320
CGGTGTGTTA  TCTCACATTT  GATCAGAGAG  CATGATCTCT  CTTAACAGAC  CTGCCACCCT   4380
AATCAACGGG  AGTGCTCACA  CAAGTGGGAG  TCTGAGAGCT  TAGCCCTATG  CCCACCCTGG   4440
```

( 2 ) INFORMATION FOR SEQ ID NO:5:

( i ) SEQUENCE CHARACTERISTICS:

(A) LENGTH: 50 amino acids
(B) TYPE: amino acid
(D) TOPOLOGY: linear (ii) MOLECULE TYPE: protein (xi) SEQUENCE DESCRIPTION: SEQ ID NO:5:

```
Met Thr Cys Lys Met Ser Gln Leu Glu Arg Asn Ile Glu Thr Ile Ile
 1               5                  10                  15
Asn Thr Phe His Gln Tyr Ser Val Lys Leu Gly His Pro Asp Thr Leu
            20                  25                  30
Asn Gln Gly Glu Phe Lys Glu Leu Val Arg Lys Asp Leu Gln Asn Phe
        35                  40                  45
Leu Lys
    50
```

(2) INFORMATION FOR SEQ ID NO:6:

(i) SEQUENCE CHARACTERISTICS:
(A) LENGTH: 64 amino acids
(B) TYPE: amino acid
(D) TOPOLOGY: linear (ii) MOLECULE TYPE: protein (xi) SEQUENCE DESCRIPTION: SEQ ID NO:6:

```
Lys Glu Asn Lys Asn Glu Lys Val Ile Glu His Ile Met Glu Asp Leu
 1               5                  10                  15
Asp Thr Asn Ala Asp Lys Gln Leu Ser Phe Glu Glu Phe Ile Met Leu
            20                  25                  30
Met Ala Arg Leu Thr Trp Ala Ser His Glu Lys Met His Glu Gly Asp
        35                  40                  45
Glu Gly Pro Gly His His His Lys Pro Gly Leu Gly Glu Gly Thr Pro
    50                  55                  60
```